(12) United States Patent
Metzner et al.

(10) Patent No.: US 11,554,156 B2
(45) Date of Patent: Jan. 17, 2023

(54) PHARMACEUTICAL FORMULATIONS OF C1 ESTERASE INHIBITOR

(71) Applicant: CSL BEHRING GMBH, Marburg (DE)

(72) Inventors: Hubert Metzner, Marburg (DE); Ernst-Juergen Kanzy, Weimar (DE)

(73) Assignee: CSL BEHRING GMBH, Marburg (DE)

( * ) Notice: Subject to any disclaimer, the term of this patent is extended or adjusted under 35 U.S.C. 154(b) by 7 days.

(21) Appl. No.: 16/932,919

(22) Filed: Jul. 20, 2020

(65) Prior Publication Data

US 2020/0390845 A1    Dec. 17, 2020

Related U.S. Application Data

(63) Continuation of application No. 16/323,155, filed as application No. PCT/EP2017/069765 on Aug. 4, 2017, now abandoned.

(30) Foreign Application Priority Data

Aug. 5, 2016  (EP) ..................................... 16183030

(51) Int. Cl.
| | |
|---|---|
| A61K 38/00 | (2006.01) |
| A61K 9/00 | (2006.01) |
| A61K 47/26 | (2006.01) |
| A61K 38/55 | (2006.01) |
| A61K 9/19 | (2006.01) |
| A61K 47/02 | (2006.01) |
| A61K 47/10 | (2017.01) |
| A61K 47/18 | (2017.01) |
| A61K 47/22 | (2006.01) |
| A61K 47/24 | (2006.01) |

(52) U.S. Cl.
CPC .......... *A61K 38/005* (2013.01); *A61K 9/0019* (2013.01); *A61K 9/19* (2013.01); *A61K 38/55* (2013.01); *A61K 47/02* (2013.01); *A61K 47/10* (2013.01); *A61K 47/183* (2013.01); *A61K 47/22* (2013.01); *A61K 47/24* (2013.01); *A61K 47/26* (2013.01)

(58) Field of Classification Search
CPC .... A61K 38/005; A61K 9/0019; A61K 47/26; A61K 38/55; A61K 9/19; A61K 47/02; A61K 47/10; A61K 47/183; A61K 47/22; A61K 47/24

See application file for complete search history.

(56) References Cited

U.S. PATENT DOCUMENTS

| | | | |
|---|---|---|---|
| 4,915,945 A | 4/1990 | Pelzer et al. | |
| 5,939,389 A | 8/1999 | Eisele et al. | |
| 6,248,365 B1 | 6/2001 | Römisch et al. | |
| 6,875,432 B2 | 4/2005 | Liu et al. | |
| 7,053,176 B1 | 5/2006 | Häfner et al. | |
| 7,067,713 B2 | 6/2006 | Nuijens et al. | |
| 8,283,319 B2 | 10/2012 | Schulte et al. | |
| 9,352,016 B2 | 5/2016 | Zeitler et al. | |
| 9,518,127 B2 | 12/2016 | Panousis et al. | |
| 9,616,111 B2 | 4/2017 | Ruddy et al. | |
| 9,624,307 B2 | 4/2017 | Nahrendorf et al. | |
| 9,856,325 B2 | 1/2018 | Panousis et al. | |
| 9,856,326 B2 | 1/2018 | Panousis et al. | |
| 9,957,329 B2 | 5/2018 | Meuth et al. | |
| 9,987,328 B2 | 6/2018 | Zeitler et al. | |
| 10,286,047 B2 | 5/2019 | Spirig et al. | |
| 10,471,142 B2 | 11/2019 | Basta et al. | |
| 2014/0234293 A1 | 8/2014 | Basta et al. | |
| 2016/0008442 A1 | 1/2016 | Spirig et al. | |
| 2016/0166660 A1 | 6/2016 | Nolte et al. | |
| 2018/0036394 A1 | 2/2018 | Schaefer et al. | |
| 2019/0175683 A1 | 6/2019 | Metzner et al. | |
| 2019/0183991 A1 | 6/2019 | Machnig et al. | |
| 2019/0269766 A1 | 9/2019 | Spirig et al. | |
| 2020/0129600 A1 | 4/2020 | Nolte et al. | |

FOREIGN PATENT DOCUMENTS

| | | |
|---|---|---|
| GB | 2530921 | 4/2016 |
| WO | WO 2006/128497 A1 | 12/2006 |
| WO | WO 2007/073186 A2 | 6/2007 |
| WO | WO 2011/109365 A2 | 9/2011 |
| WO | WO 2014/145519 A2 | 9/2014 |
| WO | WO 2015/173782 A1 | 11/2015 |
| WO | WO 2016/131958 A1 | 8/2016 |

OTHER PUBLICATIONS

DrugBank (2015).*
European Medicines Agency, Summary of Product Characteristics for Ruconest®, first version published Aug. 11, 2010 (23 pages).
European Medicines Agency, Summary of Product Characteristics for Velcade®, first version published Feb. 12, 2009 (106 pages).
European Medicines Agency, Public Assessment Report for Cinryze®, Procedure n° EMEA H / C / 001207, first published on Jul. 15, 2011 (64 pages).
European Medicines Agency Committee for Proprietary Medicinal Products, Note for Guidance on Maximum Shelf-Life for Sterile Products for Human Use After First Opening or Following Reconstitution, London, Jan. 28, 1998 (2 pages).
Manning, M. C. et al., "Stability of Protein Pharmaceuticals: An Update," *Pharmaceutical Research*, 2020; 27(4): 544-575.
Mateos, M. et al., "Safety and efficacy of subcutaneous formulation of bortezomib versus the conventional intravenous formulation in multiple myeloma," 2012, *Therapeutics Advances in Hematology*, 3(2) 117-124.
Material Safety Data Sheet for Berinert®, CSL Behring, Date of issue: Sep. 23, 2009 (5 pages).

(Continued)

*Primary Examiner* — Shirley V Gembeh (74) *Attorney, Agent, or Firm* — Finnegan, Henderson, Farabow, Garrett & Dunner, LLP (57) ABSTRACT

The present invention relates to pharmaceutical formulations comprising the C1 esterase inhibitor (C1-INH), exhibiting a higher stability for prolonged storage and a reduced formation of aggregates of said esterase inhibitor (C1-INH) upon storage for ameliorated use in treating or preventing disorders related to kinin formation.

16 Claims, 5 Drawing Sheets

(56) References Cited

OTHER PUBLICATIONS

Matthews, B.R. "Regulatory Aspects of Stability Testing in Europe," *Drug Development and Industrial Pharmacy*, 1999; 25(7), 831-856.
Metcalfe, J. W., "Microbiological Quality of Drug Products after Penetration of the Container System for Dose Preparation Prior to Patient Administration," *American Pharmaceutical Review*, 2009 (5 pages).
Speed Ricci, M. et al., "In-use physicochemical and microbiological stability of biological parenteral products," *Am J Health-Syst Pharm*, 2015; 72: 396-407.
Gamble, C. N., "The Role of Soluble Aggregates in the Primary Immune Response of Mice to Human Gamma Globulin", 1966, Int. Arch. Allergy, vol. 30, No. 5, pp. 446-455.
Bock, S. C. et al., "Human C1 Inhibitor: Primary Structure, cDNA Cloning, and Chromosomal Localization", 1986, Biochem., vol. 25, No. 15, pp. 4292-4301.
Dintzis, R. Z. et al., "The Immunogenicity of Soluble Haptenated Polymers is Determined by Molecular Mass and Hapten Valence", 1989, J Immunol., vol. 143, No. 4, pp. 1239-1244.
Bachmann, M. F. et al., "The Influence of Antigen Organization on B Cell Responsiveness", 1993, Science, vol. 262, No. 5138, pp. 1448-1451.
Cleland, J. L. et al., "The Development of Stable Protein Formulations: A Close Look at Protein Aggregation, Deamidation, and Oxidation", 1993, Critical Reviews in Therapeutic Drug Carrier Systems, vol. 10, No. 4, pp. 307-377.
Bachmann, M. F. et al., "Neutralizing Antiviral B Cell Responses", 1997, Annu. Rev. Immunol., vol. 15, pp. 235-270.
Österberg, T. et al., "Development of a Freeze-Dried Albumin-Free Formulation of Recombinant Factor VIII SQ", 1997, Pharmaceutical Research, vol. 14, No. 7, pp. 892-898.
Caliezi, C. et al., "C1-Esterase Inhibitor: An Anti-Inflammatory Agent and Its Potential Use in the Treatment of Diseases Other Than Hereditary Angioedema", 2000, Pharmacological Reviews, vol. 52, No. 1, pp. 91-112.
Akita, N. et al., "Protective Effect of C1 Esterase Inhibitor on Reperfusion Injury in the Rat Middle Cerebral Artery Occlusion Model", Feb. 2003, Neurosurgery, vol. 52, No. 2, pp. 395-401.
Chen, B. et al., "Influence of Histidine on the Stability and Physical Properties of a Fully Human Antibody in Aqueous and Solid Forms", Dec. 2003, Pharmaceutical Research, vol. 20, No. 12, pp. 1952-1960.
De Simoni, M. G. et al., "Neuroprotection by Complement (C1) Inhibitor in Mouse Transient Brain Ischemia", 2003, J. Cereb. Blood Flow Metab., vol. 23, No. 2, pp. 232-239.
Seong, S.-Y. et al., "Hydrophobicity: An Ancient Damage Associated Molecular Pattern that Initiates Innate Immune Responses", Jun. 2004, Nature Reviews | Immunology, vol. 4, No. 6, pp. 469-478.
Shire, S. J. et al., "Challenges in the Development of High Protein Concentration Formulations", Jun. 2004, J. of Pharm. Sci., vol. 93, No. 6, pp. 1390-1402.
Davis III, A. E., "The pathophysiology of hereditary angioedema", 2005, Clin. Immunol., vol. 114, pp. 3-9.
Tian, F. et al., "Calorimetric Investigation of Protein/Amino Acid Interactions in the Solid State", 2006, Int. J. Pharmaceut. vol. 310, pp. 175-186.
Wakankar, A. A. et al., "Formulation Considerations for Proteins Susceptible to Asparagine Deamidation and Aspartate Isomerization", Nov. 2006, J. Pharm. Sci., vol. 95, No. 11, pp. 2321-2336.
Cicardi, M. et al., "The Use of Plasma-Derived C1 Inhibitor in the Treatment of Hereditary Angioedema", 2007, Expert Opin. Pharmacother., vol. 8, No. 18, pp. 3173-3181.
Tian, F. et al., "Spectroscopic Evaluation of the Stabilization of Humanized Monoclonal Antibodies in Amino Acid Formulations", 2007, Int. J. of Pharmaceutics., vol. 335, pp. 20-31.
Bork, K., "Diagnosis and Treatment of Hereditary Angioedema with Normal C1 Inhibitor", 2010, Allergy, Asthma & Clinical Immunology, vol. 6, No. 15, pp. 1-8.
Longhurst, H. et al., "Hereditary Angio-Oedema", 2012, Lancet, vol. 379, pp. 474-481.
Narhi, L. O. et al., "Classification of Protein Aggregates", Feb. 2012, J. of Pharm. Sci., vol. 101, No. 2, pp. 493-498.
Karnaukhova, E., "C1-Esterase Inhibitor: Biological Activities and Therapeutic Applications", 2013, J. Hematol. Thromb. Dis., vol. 1, No. 3, pp. 1-7.
Feussner, A. et al., "Biochemical Comparison of Four Commercially Available C1 Esterase Inhibitor Concentrates for Treatment of Hereditary Angioedema", Oct. 2014, Transfusion., vol. 54, pp. 2566-2573.
European Patent Office, European Search Report, dated Jan. 26, 2017, for European Patent Application No. 16183030.2, 8 pages.
European Patent Office, International Search Report and Written Opinion, dated Oct. 19, 2017, for PCT Patent Application No. PCT/EP2017/069765, 11 pages.
Ruddy S. et al.
Schranz J., Declaration dated Mar. 23, 2016, excerpted from the prosecution history of U.S. Pat. No. 9,616,111.
Frank M. M., Declaration dated Feb. 23, 2016, excerpted from the prosecution history of U.S. Pat. No. 9,616,111.
Schranz J. et al., "Safety, Pharmacokinetics (PK), and Pharmacodynamics (PD) of Subcutaneous (SC) CINRYZE® (C1 Esterase Inhibitor [Human]) with Recombinant Human Hyaluronidase (rHuPH20) in Subjects with Hereditary Angioedema (HAE)," ViroPharma Incorporated (2012), Poster L21 presented at the American Academy of Allergy, Asthma & Immunology annual meeting.
Schranz J. et al., "Safety, Pharmacokinetics (PK), and Pharmacodynamics (PD) of Subcutaneous (SC) CINRYZE® (C1 Esterase Inhibitor [Human]) with Recombinant Human Hyaluronidase (rHuPH20) in Subjects with Hereditary Angioedema (HAE)," J. Allergy Clin. Immunol, vol. 129, Abstract L21, 2012.
Jiang H. et al., "Subcutaneous Infusion of Human C1 Inhibitor in Swine", Clinical Immunology, (2010), vol. 136, pp. 323-328.
Gatlin L. A., "Formulation and Administration Techniques to Minimize Injection Pain and Tissue Damage Associated with Parenteral Products," Injectable Drug Development—Techniques to Reduce Pain and Irritation, (1999), pp. 401-421.
Zuraw B. L. et al., "Nanofiltered C1 Inhibitor Concentrate for Treatment of Hereditary Angioedema," The New England Journal of Medicine, (2010), vol. 363, No. 6, pp. 513-522.
Levi M. et al., "Self-administration of C1-inhibitor concentrate in patients with hereditary or acquired angioedema caused by C1-inhibitor deficiency," The Journal of Allergy and Clinical Immunology, (2006), vol. 117, No. 4, pp. 904-908.
Cinryze® Label—Prescribing Information, Nov. 2012, pp. 1-2.
Craig, T., Declaration dated May 31, 2017.
Machnig T. and Waldhauser H., Declaration dated May 18, 2016.
Metzner H., Declaration dated May 24, 2017.
Roberts C. J., Declaration dated May 29, 2017.
Connolly B. D. et al., "Weak Interactions Govern the Viscosity of Concentrated Antibody Solutions: High-Throughput Analysis Using the Diffusion Interaction Parameter," Biophysical Journal, (2012), vol. 103, pp. 69-78.
Sardana N. et al., "Recent Advances in Management and Treatment of Hereditary Angioedema," Pediatrics, (2011), vol. 128, No. 6, pp. 1173-1180.
"A Study to Evaluate the Clinical Efficacy and Safety of Subcutaneously Administered C1-esterase Inhibitor in the Prevention of Hereditary Angioedema," Clinicaltrials.gov, NCT0191256.
"Subcutaneous CINRYZE With Recombinant Human Hyaluronidase for Prevention of Angioedema Attacks," Clinicaltrials.gov, NCT01756157, start date Dec. 2012.
"Berinert P Study of Subcutaneous versus Intravenous Administration (PASSION)," Clinicaltrials.gov, NCT00748202.
Jolles, S. et al., "New Frontiers in Subcutaneous Immunoglobulin Treatment", Biol. Ther., (2011), pp. 1-15.
Informed Consent Form for Enrollment for Adults for CSL830_2001, CSL Behring GmbH, US site: Hershey Medical Center, Hershey, PA, Version date: Jul. 9, 2012.
Craig, T. et al., "WAO Guideline for the Management of Hereditary Angioedema", WOA Journal, (2012), pp. 182-199.

(56) References Cited

OTHER PUBLICATIONS

CSL Behring Initiates Study of Subcutaneous Administration of C1-esterase Inhibitor in Patients with Hereditary Angioedema, CSL News Release, May 3, 2012.
ViroPharma and Halozyme Therapeutics Announce Initiation of Phase 2b Dose Ranging Combination Study for Subcutaneous Administration of Cinryze (C1 esterase inhibitor [human]) With Hyaluronidase (rHuPH20), Press release, Dec. 19, 2012.
Over, J. et al., "C1-Inhibitor" in "Production of Plasma Proteins for Therapeutic Use", Wiley & Sons (2013), Chapter 17, pp. 241-258.
Riedl, et al. "Subcutaneous administration of human C1 inhibitor with recombinant human hyaluronidase in patients with hereditary angioedema," Allergy Asthma Proc., vol. 27, pp. 489-500 (2016).
Berinert FDA Approval Letter, Oct. 9, 2009.
Longhurst, H.J., et al., "C1-Inhibitor Concentrate Home Therapy for Hereditary Angioedema: A Viable, Effective Treatment Option", Clin. & Exp. Immunol., vol. 147, pp. 11-17, (2006).
Myers, J.K. et al., "Denaturant m Values and Heat Capacity Changers: Relation to Changers in Accessible Surface Areas of Protein Unfolding," Protein Science, vol. 4, pp. 2138-2148 (1995).
CINRYZE Approval Letter, Oct. 10, 2008.
"Subcutaneous CINRYZE With Recombinant Human Hyaluronidase for Prevention of Angioedema Attacks," Clinicaltrials.gov, NCT01756157.
Gomella, L.G., et al., Clinician's Pocket Reference, $9^{th}$ Ed. (2002).
Cinryze® FDA Briefing Document, Blood Products Advisory Committee Meeting, May 1-2, 2008.
Firszt, R. et al, "An Overview of Novel Therapies for acute Hereditary Angioedema", Am. J. Clin. Derm., vol. 11, pp. 371-443 (2010).
Frank, M. M. "Recombinant and Plasma-Purified Human C1 Inhibitor for the Treatment of Hereditary Angioedema," WAO Journal, Supplement (2010).
Ghannam, A. "C1 Inhibitor as a Glycoprotein: The Influence of Polysaccharides on its Function and Autoantibody Target," Mol. Imm., vol. 71, pp. 161-165 (2016).
European Medicines Agency, Jun. 24, 2010, EMA/CHMP/450053/2010, Evaluation of Medicines for Human Use, CHMP Assessment Report, Ruconest®, Procedure No. EMEA/H/C/001223.
Harrison, R.A. "Human C1 Inhibitor: Improved Isolation and Preliminary Structural Characterization," Biochem., vol. 22, pp. 5001-5007 (1983).
Hossler, P. et al., "Optimal and Consistent Protein Glycosylation in Mammalian Cell Culture," Glycobiology, vol. 19, pp. 936-949 (2009).
Shire, S. J. "Formulation and Manufacturability of Biologics," Current Opinion in Biotech., vol. 20, pp. 708-714 (2009).
Lis, H. et al., "Protein Glycosylation Structural and Functional Aspects," Eur. J. Biochem., vol. 218, pp. 1-27 (1993).
Longhurst, H. J. et al., "HAE International Home Therapy Consensus Document," Allergy, Asthma & Clinical Immunol., vol. 6, pp. 1-7 (2010).
Martinez-Saguer, M. et al., "Pharmacokinetic Berinert P Study of Subcutaneous Versus Intravenous Administration In Subjects with Moderate Hereditary Angioedema—The Passion Study", J. Allergy Clin. Immunol., vol. 127 (2011), Abstract 389.
Martinez-Saguer, M. et al., "Pharmacokinetic Berinert Study of Subcutaneous Versus Intravenous Administration in Patients with Moderate Hereditary Angioedema—The PASSION Study", Poster 389, (2011).
Martinez-Saguer, M. et al., "Pharmacokinetics of Plasma-Derived C1-Esterase Inhibitor After Subcutaneous Versus Intravenous Administration in Subjects with Mild or Moderate Hereditary Angioedema: The PASSION Study," Transfusion, vol. 54, Jun. 2014.
Monkos, K., "Viscometric Study of Human, Bovine, Equine and Ovine Haemoglobin in Aqueous Solution," Int. J. Bio. Macromol., vol. 16, pp. 31-35 (1994).
Monkos, K., "Viscosity of Bovine Serum Albumin Aqueous Solutions as a Function of Temperature and Concentration," Int. J. Bio. Macromol., vol. 18, pp. 61-68 (1996).

Monkos, K., "Concentration and Temperature Dependence of Viscosity in Lysozyme Aqueous Solutions," Biochimica et Biophysica Acta, vol. 1339, pp. 304-310 (1997).
Monkos, K., "Viscosity Analysis of the Temperature Dependence of the Solution Conformation of Ovalbumin," Biophysical Chemistry, vol. 85, pp. 7-16, (2000).
Nilsson, T. et al., "Purification and Characterization of Human C1-Esterase Inhibitor", Biochimica et Biophysica Acta, vol. 705, pp. 271-276 (1982).
Perkins, J. et al., "Two-Domain Structure of the Native and Reactive Centre Cleaved Forms of C1 Inhibitor of Human Complement by Neutron Scattering," J. Mol. Biol., vol. 214, pp. 751-763 (1990).
Reuter, G. et al., "Eukaryotic Glycosylation: Whim of Nature or Multipurpose Tool?," CMLS, vol. 55, pp. 368-422 (1999).
"Roche's Herceptin given by subcutaneous injection offers greater convenience to patients and reduces overall healthcare costs compared to standard IV infusion," Press Release pp. 1-5, Mar. 23, 2012.
Weiss et al., "Principles, Approaches, and Challenges for Predicting Protein Aggregation Rates and Shelf Life," J. Pharm. Sci., vol. 98, pp. 1246-1277 (2009).
Schellekens, H., "Why Some Proteins Have Sugars? Epoetins, from Alfa to Zeta," EJHPP, vol. 14, pp. 29-34 (2008).
Shalaev, E. et al., "Thermophysical Properties of Pharmaceutically Compatible Buffers at Sub-Zero Temperatures: Implications for Freeze-Drying," Pharm. Res., vol. 19, pp. 115-216 (2002).
Sola, R.J. et al., "Effects of Glycosylation on the Stability of Protein Pharmaceuticals," J. Pharm. Sci., vol. 98, pp. 1223-1245 (2009).
"CSL Behring announces completion of national marketing authorizations to Berinert® after MRP in 23 European countries," CSL News Release, May 27, 2010.
"ViroPharma Announces Completion of Enrollment in Phase 2 Study Evaluating Subcutaneous Delivery of Cinryze (C1 Esterase Inhibitor [Human])," Press Release, Oct. 25, 2010.
Vivaglobin® Prescribing Information, CSL Behring, Apr. 2010.
Vugmeyster, X. X. et al., "Pharmacokinetics and Toxicology of Therapeutic Proteins: Advances and Challenges," World J. Biol. Chem., vol. 3, pp. 73-92 (2012).
Wang, W., "Protein Aggregation and its Inhibition in Biopharmaceutics," Intl. J. Pharm., vol. 289, pp. 1-30 (2005).
Yadav, S. et al., "Viscosity Analysis of High Concentration Bovine Serum Albumin Aqueous Solutions," Pharm. Res., vol. 281, pp. 1973-1983 (2011).
United Kingdom Patent Application No. 1519921.9, Shire Reply dated Mar. 2, 2017.
Jiang, H. at al., Subcutaneous (SQ) versus intravenous (IV) infusion of C1 Inhibitor (inh) on blood levels in swine, $6^{th}$ C1 Inhibitor Deficiency Workshop 46 (May 2009).
Informed Consent Form for Enrollment for Adults for CSL830_2001, CSL Behring GmbH, Germany site: Johann Wolfgang Goethe University Hospital, Frankfurt, Germany.
"ViroPharma Provides Update on Phase 2 Clinical Evaluation of Subcutaneous Cinryze® (C1 Esterase Inhibitor [human]) with Recombinant Human Hyaluronidase (rHuPH20)," Press Release, Aug. 1, 2012.
Longhurst, H. et al., "Prevention of Hereditary Angioedema Attacks with a Subcutaneous C1 Inhibitor," New Eng. J. Med., vol. 376, pp. 1131-1140 (2017).
Berinert 500 IU, Summary of Product Characteristics Sep. 2, 2015.
Brackertz, D. et al., "Hereditary Angioneurotic Oedema," The Lancet, vol. 2 (1973).
European Patent Application No. 14762343.3, Shire Reply dated Mar. 2, 2017.
Zuraw, B. L. et al., "Phase II Study of Results of a Replacement Therapy for Hereditary Angioedema with Subcutaneous C1-Inhibitor Concentrate," Allergy, vol. 70, pp. 1319-1328 (2015).
Latypov, R. F. et al., "Elucidation of Acid-Induced Unfolding and Aggregation of Human Immunoglobulin IgG1 and IgG2 Fc," J. Biol. Chem., vol. 287, pp. 1381-1396 (2012).
Li, H. H., "Self-Administered C1 Esterase Inhibitor Concentrates for the Management of Hereditary Angioedema: Usability and Patient Acceptance," Patient Preference and Adherence, vol. 10, pp. 1727-1737 (2016).

(56) References Cited

OTHER PUBLICATIONS

Spath, P. J. et al., "Quantification of C1-Inhibitor Functional Activities by Immunodiffusion Assay in Plasma of Patients with Hereditary Angioedema Evidence of a Functionally Critical Level of C1-Inhibitor Concentration," Complement, vol. I, pp. 147-159 (1984).
EPO Patent Application No. EP 14 762 343.3, Decision to Grant dated Jun. 1, 2017.
Fathallah, A. M. et al., "Anatomical, Physiological and Experimental Factors Affecting the Bioavailability of SC Administered Large Biotherapeutics," J. Pharm. Sci., vol. 104, pp. 301-306 (2015).
McLennan, D. N. et al., "Subcutaneous Drug Delivery and the Role of the Lymphatics," Drug Discovery Today: Tech., vol. 2, pp. 89-96 (2005).
Am. Acad. of Allergy, Asthma & Immunology, Final Program, 2012 Annual Meeting (2012).
129(2) J. Allergy & Clin. Immunol. (Supplement) (Feb. 2012).
"A Study to Evaluate the Clinical Pharmacology and Safety of C1-Esterase Inhibitor Administered by the Subcutaneous Route," Clinicaltrials.gov, NCT01576523, first posted Apr. 12, 2012.
"A Study to Evaluate the Safety and Pharmacokinetics of Two Formulations of C1-Esterase Inhibitor," NCT01760343, first posted Jan. 4, 2013.
Opposition against European Patent EP-B-2 968 434, Notice of Opposition, by CSL Behring GmbH, Mar. 28, 2018.
"Subcutaneous Cinryze with rHuPH20 produces positive effects in prevention of HAO," BMI Research, Mar. 6, 2012.
Richter W. F. et al., (2012), The AAPS Journal, 14(3): 559-570, "Mechanistic Determinants of Biotherapeutics Absorption Following SC Administration."
European Medicines Agency, Jul. 25, 2013, CHMP assessment report for paediatric use studies submitted according to Article 46 of the Regulation (EC) No. 1901/2006, Procedure No. EMA/H/C/001207/A46/0015.1.
Berinert, EU Summary of Product Characteristics, Apr. 18, 2012.
Berinert Prescribing Information, CSL Behring, Approved 2009.
Cinryze Summary of Product Characteristics, first authorized Jun. 15, 2011.
Zuraw, B. L., "HAE Therapies: Past Present and Future," Allergy, Asthma, Clin. Immunol., vol. 6, pp. 1-8(2010).
Cardona, L. P. et al., "Recent Developments in the Treatment of Acute Abdominal and Facial Attacks of Hereditary Angioedema: Focus on Human C1 Esterase Inhibitor," Application of Clinical Genetics, vol. 3, pp. 133-146 (2010).
Viropharma Inc. Investor Day, "Broadening Horizons," Sep. 21, 2012.
Martinez-Saguer, M., Pharmacokinetics of plasma-derived C1-Esterase Inhibitor after Subcutaneous Versus Intravenous Administration in Patients with Moderate Hereditary Angioedema, Presentation, Frankfurt am Main, Germany.
Martinez-Saguer, M. et al., "Pharmacokinetics of Plasma-Derived C1-Esterase Inhibitor After Subcutaneous Versus Intravenous Administration in Subjects with Mild or Moderate Hereditary Angioedema," Abstract, European Academy of Allergy and Clin. Immunol., Istanbul, Turkey, Jun. 11-15, 2011.
Cinryze Study Synopsis, Viropharma Inc., Sep. 6, 2011.
Van Doorn, M., et al. "A Phases I Study of Recombinant Human C1 Inhibitor in Asymptomatic Patients with Hereditary Angioedema," J. Allergy Clin. Immunol., vol. 116, pp. 876-883 (2005).
Tourangeau, L. M., et al., "The New Era of C1-Esterase Inhibitor Deficiency Therapy," Curr. Allergy, Asthma Rep., vol. 11, pp. 345-351 (2011).
CSL Behring v. Shire ViroPharma Inc., Petition for Inter Partes Review, IPR2017-01512, May 31, 2017.
CSL Behring v. Shire ViroPharma Inc., Final Written Decision, IPR2017-01512, Dec. 7, 2017.
Shire Viropharma Inc. v. CSL Behring LLC, First Amended Complaint, 1:17-cv-00414, Apr. 28, 2017.
Shire Viropharma Inc. v. CSL Behring LLC, Defendant's Answer and Counterclaims, 1:17-cv-00414, Jan. 26, 2018.

Opposition of European Patent EP2968434B1, Reply of Patent Proprietor to Notice of Opposition, Shire Viropharma, Aug. 21, 2018.
Opposition of European Patent EP2968434B1, Notice of Opposition, Octopharma AG, Mar. 28, 2018.
The Pharmaceutics and Compounding Laboratory (2010); "Subcutaneous," UNC.
Extracts from Ansel's Pharmaceutical Dosage Forms and Drug Delivery Systems, ninth edition; Chapter 5, pp. 162-170; 2001.
Austria Codex Fachinformation 1997/1998; pp. 355-366 and 469 ; (Berinert P).
Lunn et al., "Cinryze as the first approved C1 inhibitor in the USA for the treatment of hereditary angioedema: approval, efficacy and safety," J. Blood Medicine, 2010; 1; 163-170.
Drouet et al., "A sensitive method to assay blood complement C1 Inhibitor activity," Clinica Chimica Acta, 174:121-130, 1988.
Burckbuchler et al., "Rheological and syringeability properties of highly concentrated human polyclonal immunoglobulin solutions," European Journal of Pharmaceuticals and Biopharmaceutics, 2010; 76: 351-356.
CINRYZE Highlights of prescribing information.
European Pharmacopoeia Fourth Edition, Sep. 20, 2001 (Human Albumin Solution).
De Serres et al., "Safety and efficacy of pasteurized C1 inhibitor concentrate (Berinert P) in hereditary angioedema: a review," Transfusion and Apheresis Science, 29:27-254, 2003.
Daugherty et al., "Formulation and delivery issues for monoclonal antibody therapeutics," Advanced Drug Delivery Reviews, 58: 686-706, 2006.
Frost G. I., "Recombinant human hyaluronidase (rHuPH20): an enabling platform for subcutaneous drug and fluid administration," Expert Opin. Drug Deliv., 4(4):427-440, 2007.
"Viropharma Licenses Halozyme's Hyaluronidase for $9M to Develop Subcutaneous Cinryze" https://www.genengnews.com/gen-new-highlights/viropharma-licenses-halozymes-hyaluronidase-for-9m-to-develop-subcutaneous-cinryze/81245135 (downloaded Aug. 15, 2018).
Dunn A. et al., "Hyaluronidase: a review of approved formulations, indications and off-label use in chronic pain management," Expert Opinion on Biological Therapy, 10:127-131, 2010.
Shapiro R., "Subcutaneous Immunoglobulin Therapy by Rapid Push is Preferred to Infusion by Pump: A Retrospective Analysis," J. Clin. Immunol., 30:301-307, 2010.
Sasson M. et al., "Hypodermoclysis: An Alternative Infusion Technique," American Family Physician, 64(9): 1575-1578, 2001.
Haller M.F., "Converting Intravenous Dosing to Subcutaneous Dosing With Recombinant Human Hyaluronidase," Pharmaceutical Technology, 31(10), 2007.
Kling J., "Highly concentrated protein formulations: Finding solutions for the next generation of parenteral biologics", (http://www.bioprocessintl.com/manufacturing/formulation/highly-concentrated-protein-formulations-351576/) BioProcess International, 2014.
Courthadon J. et al., "Covalent binding of glycosyl residues to bovine casein: effects on solubility and viscosity," J. Agric. Food Chem., 37:32-36, 1989.
Boylan et al., "Parenteral Products," Modern Pharmaceuticals (Marcel Dekker), Chapter 12:381-414, 2002.
Shapiro R.S., "Subcutaneous immunoglobulin: rapid push vs. infusion pump in pediatrics," Pediatric Allergy Immunol., 24:49-53, 2013.
Kramer R.M. et al., "Toward a molecular understanding of protein solubility: Increased negative surface charge correlates with increased solubility," Biophysical Journal, 102:1907-1925, 2012.
Georgiou G. et al., "Folding and aggregation of TEM ß-lactamase: Analogies with the formation of inclusion bodies in *Eschrichia coli*," Protein Science, 3:1953-1960, 1994.
Alford J.R. et al., "High Concentration Formulation of Recombinant Human Interleukin-1 Receptor Antagonist: II. Aggregation Kinetics," Journal of Pharm. Sciences, 97(8): 3005-3021, 2007.
Yadav S. et al., "Factors Affecting the Viscosity in High Concentration Solutions of Different Monoclonal Antibodies," Journal of Pharm. Sciences, 99(12): 4812-4829, 2010.
Jezek J. et al.,(2011), Advanced Drug Delivery Reviews, 63(13):1107-1117, "Viscosity of concentrated therapeutic protein compositions."

(56) References Cited

OTHER PUBLICATIONS

Baniel A. et al., (1992), J. Agric. Food Chem., 40:200-205, "Functional properties of glycosylated derivatives of the 11S storage protein from Pea (*Pisum sativum* L.)."

"Polysorbate 80" DrugBank https://www.drugbank.ca/drugs/DB1106 (2015).

U.S. Appl. No. 16/323,155, Non-Final Office Action dated Jan. 21, 2020, (9 pages).

* cited by examiner

PHARMACEUTICAL FORMULATIONS OF C1 ESTERASE INHIBITOR

This application is a continuation of application Ser. No. 16/323,155, having a 35 U.S.C. § 371(c) date of Feb. 4, 2019, which is the national stage entry under 35 U.S.C. § 371 of International Application No. PCT/EP2017/069765, filed Aug. 4, 2017, which claims priority to European Patent Application No. 16183030.2, filed Aug. 5, 2016. The contents of these applications are each incorporated herein by reference in their entirety.

FIELD OF INVENTION

The present invention relates to pharmaceutical formulations comprising the C1 esterase inhibitor ("C1-INH"), exhibiting reduced formation of aggregates of said esterase inhibitor (C1-INH) upon storage.

BACKGROUND

C1-INH, a plasma glycoprotein with a molecular weight of 104 kDa, belongs to the protein family of serine protease inhibitors (serpins), which regulate the activity of serine proteases by inhibiting their catalytic activity (Bock S C, et al., Biochemistry 1986, 25: 4292-4301). C1-INH inhibits the classical pathway of the complement system by inhibiting the activated serine proteases C1s and C1r. Furthermore, C1-INH is a major inhibitor of the contact activation system due to its ability to inhibit the activated serine proteases factor XIIa (FXIIa), factor XIa (FXIa), and plasma kallikrein (Davis A E, Clin. Immunol. 2005, 114: 3-9; Caliezi C et al., Pharmacol. Rev. 2000, 52: 91-112). Deficiency in C1-INH leads to the clinical manifestation of hereditary angioedema (HAE), which is characterized by episodes of acute angioedema attacks in subcutaneous or submucosal tissues such as the skin, larynx, or visceral organs (Longhurst H, et al. Lancet 2012, 379: 474-481) which last between 1 and 7 days and occur at irregular intervals. Abnormalities in C1-INH plasma content or in its functional activity (often referred to as a deficiency of functional C1-INH) result from various large and small mutations in the C1-INH gene (vide supra) (Karnaukhova E, J. Hematol. Thromb. Dis., 2013, 1-7).

Two types of hereditary C1-INH deficiency generally exist. The more prevalent type I HAE is characterized by low content (below 35% of normal) and low inhibitory activity of C1-INH in the circulation. Type II HAE is associated with normal or elevated antigenic levels of C1-INH of low functional activity. Recently, HAE with normal C1-INH (also known as type III HAE) has been described in two subcategories: (1) HAE due to mutation in the factor XII gene and, as a result, increased activity of factor XII leading to a high generation of bradykinin, and (2) HAE of unknown genetic cause. HAE attacks can be treated effectively by administering C1-INH (Longhurst H, et al., Lancet 2012, 379: 474-481; Bork K, Allergy Asthma Clin. Immunol. 2010, 6: 15). Moreover, administration of C1-INH has been shown to prevent edema formation in patients when given prophylactically. C1-INH is currently marketed as. e.g. Berinert® (CSL Behring). Due to its inhibitory effects on the complement and the contact activation systems, C1-INH substitution restores normal homeostatic function and inhibits the excessive formation of vasoactive peptides such as bradykinin, which mediate the formation of angioedema.

C1-INH has been reported to reduce ischemia-reperfusion injury in rodent models for cerebral ischemia-reperfusion (De Simoni et al., J Cereb Blood Flow Metab. 2003, 23: 232-9; Akita et al., 2003, Neurosurgery 52: 395-400).

The C1-INH compositions commercially available for the treatment of C1-Inh deficiency up to date are all large volume formulations, i.e., these formulations must be administered by intravenous injection. In view of the fact that C1-INH has been shown to prevent edema formation in patients with hereditary angioedema when given prophylactically (Cicardi M et al., Expert Opin. Pharmacother. 2007; 8: 3173-3181), there is a requirement for formulations that can be easily self-administered by the affected patients at regular intervals.

Long-term prophylaxis of HAE aims to prevent or to minimize the number and severity of angioedema attacks. However, the medications currently available for long-term prophylaxis are in many cases not optimal. Oral antifibrinolytics requiring multiple daily doses are relatively ineffective and frequently associated with significant side effects. Anabolic androgens are convenient to take and usually effective at doses <200 mg/day but can be associated with significant risk of serious side effects. Currently available formulations of C1-INH require intravenous access, imposing a burden on the patient, the healthcare provider, or both.

Maintenance of intravenous access has required many patients to have ports implanted, which are associated with increased risks of infection and thrombosis. Plasma levels of functional C1-INH fall rapidly following intravenous administration of therapeutic dosages of C1-INH concentrates, reaching near basal levels within 3 days.

When manufacturing protein therapeutics, such as the C1-INH, regulatory authorities strongly recommend manufacturers of therapeutic protein products to minimize protein multimerisation and aggregation as much as possible. Moreover, an increased stability of protein therapeutics is highly desired for prolonged storage of such therapeutics. Conditions, which increase the protein's stability are also the best conditions to prevent denaturation and formation of high molecular weight components (HMWC) by multimerisation and aggregation, in particular of the therapeutic protein.

Therefore, strategies that minimize HMWC formation are highly desired to be developed as early as feasible in product development. This can be achieved by e.g. using an appropriate cell substrate, selecting manufacturing conditions that minimize HMWC formation, employing a purification scheme that removes HMWC to the greatest extent possible, choosing a container system, which minimizes HMWC formation of the protein, and most notably, choosing a formulation that minimizes HMWC formation, degradation and denaturation during storage.

Hence, formulation components are principally chosen based on their ability to preserve the native conformation of the therapeutic protein by preventing denaturation due to hydrophobic interactions that may lead to HMWC formation, as well as by preventing chemical degradation, including truncation, oxidation, and deamidation (Cleland et al., Crit. Rev. Ther. Drug Carrier Syst. 1993, 10(4): 307-377; Shire et al., J. Pharm. Sci. 2004, 93(6): 1390-1402; Wakankar and Borchardt, J. Pharm. Sci. 2006, 95(11): 2321-2336).

The potential clinical consequences of immune responses induced by protein HMWC may depend on the loss or preservation of native epitopes in the HMWC: (a) some antibodies generated by the human subject against HMWC containing native protein may bind to monomeric protein as well as to the HMWC and may inhibit or neutralize product activity; (b) other antibodies to denatured/degraded and hence aggregated protein bind uniquely to the HMWC material, but not to native protein monomers (Guidance for Industry Immunogenicity Assessment for Therapeutic Protein Products, U.S. Department of Health and Human Services, Food and Drug Administration, Center for Drug Evaluation and Research (CDER), Center for Biologics Evaluation and Research (CBER), August 2014).

WO 2014/145519 discloses C1-INH compositions having about 400 or 500 U/mL C1-INH. It is suggested not to use citrate or citric acid as a buffer substance for subcutaneous administration. The disclosed formulations contain only particular buffer substances in low concentrations with no other excipient added. All disclosed C1-INH formulations have a relatively low overall purity of about 67% monomer content at $t_0$. With regard to stability the WO 2014/145519 discloses only data after one week at 40° C. and after two weeks at 25° C., i.e. no long-term stability data are shown and thus long-term stability is unproven.

In summary, there is a need for a C1-INH formulation that has a proven long-term storage stability by being less prone to HMWC formation as well as to denaturation and degradation. Furthermore, a formulation, which is easily administered in high concentrations at low volumes, is needed. In addition, it would be desirable that such a formulation can be used for prophylactic therapy as well as for acute therapy of patients suffering from hereditary angioedema.

SUMMARY

The present invention provides low volume formulations comprising high concentrations of C1-INH and having an increased C1-INH stability.

Moreover said formulations can be administered via subcutaneous injection and can easily be self-administered by the patients themselves. In addition, these formulations can also be administered via intravenous injection. In particular, the present invention provides one type of formulation, which is suitable, both for using intravenous and subcutaneous treatment, even for self-application by the patients.

Furthermore the formulations according to the invention ensure a substantially reduced formation of undesired oligomers and high molecular weight components (HMWC) compared to available C1-INH formulations.

The present invention further relates to use of such formulations in the acute and/or prophylactic treatment of disorders related to kinin formation.

The present invention further relates to kits comprising said C1-INH formulation, methods for preparing such formulations, and uses of such formulations.

In particular, the present invention relates to a stable pharmaceutical composition comprising (a) C1-INH at a concentration of about 400-2,000 IU/mL and (b) histidine, preferably L-histidine, or a salt/salts thereof at a concentration of about 5-150 mM, preferably 10-80 mM, wherein the formulation does not comprise citrate or di-hydrogen phosphate/hydrogen phosphate.

In various embodiments, the pharmaceutical formulation of the invention further comprises one or more amino acids, preferably an L-amino acid or a salt thereof at a concentration of 2-150 mM each, preferably about 5-50 mM.

In certain embodiments, the one or more amino acid is selected from arginine, glycin and lysine or any salt(s) thereof.

In various embodiments, the formulation comprises saccharose (sucrose) at a concentration of about 5-250 mM, preferably 20-200 mM.

In some embodiments, the formulation further comprises sodium chloride or sodium glutamate at a concentration of about 1-200 mM, preferably 20-150 mM.

In various embodiments the pH of the pharmaceutical formulations of this invention is between about 6.0 and 8.0, preferably between about 6.7 and 7.5.

In some embodiments, the pharmaceutical composition comprises:
(a) about 400-625 IU/mL C1-INH,
(b) about 10-200 mM sodium chloride,
(c) about 5-150 mM histidine,
(d) about 5-50 mM arginine or arginine*HCl, and
(e) about 100-200 mM saccharose.

In some embodiments, the pharmaceutical composition may further comprise
(a) a detergent selected from the group consisting of PS80 (polysorbate 80) and PS20 (polysorbate 20); and/or
(b) a preservative and/or antioxidant selected from the group consisting of benzylalcohol, cresol, phenol, methionine and glutathione.

In various embodiments, the C1-INH of this invention is human C1-INH. In preferred embodiments, the human C1-INH is derived from human plasma. Alternatively, the human C1-INH is recombinantly expressed.

In various embodiments, the pharmaceutical formulation is
(a) obtainable by reconstitution of a lyophilized powder with a suitable liquid, or
(b) provided as a liquid formulation.

In a preferred embodiment the pharmaceutical formulation is provided as a lyophilized powder.

In all of the embodiments, the formulation can be administered via subcutaneous administration or via intravenous administration whereby optionally said formulation may be self-administered by the patient.

Another aspect of the invention refers to pharmaceutical formulations for use
in the acute and/or prophylactic treatment of a disorder related to kinin formation, in particular hereditary angioedema (HAE), preferably HAE type I, HAE type II or HAE type III, secondary brain edema, edema of the central nervous system, hypotensive shock, or edema during or after contacting blood with an artificial surface;
in the acute and/or prophylactic treatment of a disorder related to an ischemia-reperfusion injury (IRI), in particular wherein the IRI is due to surgical intervention, in particular vascular surgery, cardiac surgery, neurosurgery, trauma surgery, cancer surgery, orthopedic surgery, transplantation, minimally invasive surgery, or insertion of a device for delivery of a pharmacologically active substance or for mechanical removal of complete or partial obstructions;
in the acute and/or prophylactic treatment of retinopathy; or
in preventing rejection of transplanted tissue in a patient.

Another aspect of the invention refers to kits comprising pharmaceutical formulations of the invention as a lyophilized powder and a respective volume of a suitable liquid for reconstitution. Yet another aspect of the invention refers to kits comprising the pharmaceutical formulation of the invention and at least one syringe and/or one needle. And yet another aspect refers to a syringe prefilled with a liquid pharmaceutical formulation of the invention.

DETAILED DESCRIPTION

Definitions

According to the present invention, the term "C1 esterase inhibitor" or "C1 inhibitor" ("C1-INH") refers to the proteins or fragments thereof that function as serine protease inhibitors and inhibit proteases associated with the complement system, preferably proteases C1r and C1s as well as MASP-1 and MASP-2, with the kallikrein-kinin system, preferably plasma kallikrein and/or factor XIIa, and with the coagulation system, preferably factor XIa and factor XIIa. In addition, the C1-INH can serve as an anti-inflammatory molecule that reduces the selectin-mediated leukocyte adhesion to endothelial cells. C1-INH as used herein can be the native serine protease inhibitor or an active fragment thereof, or it can comprise a recombinant peptide, a synthetic peptide, peptide mimetic, or peptide fragment that provides similar functional properties, such as the inhibition of proteases C1r and C1 s, and/or MASP-1 and MASP-2, and/or plasma kallikrein, and/or factor XIIa, and/or factor XIa. The term C1-INH shall also encompass all natural occurring alleles, splice variants and isoforms which have the same or similar functions as the C1-INH. For further disclosure regarding the structure and function of C1-INH, see U.S. Pat. Nos. 4,915,945, 5,939,389, 6,248,365, 7,053, 176 and WO 2007/073186.

One "unit" ("U") of C1-INH is equivalent to the C1-INH activity in 1 mL of fresh citrated plasma of healthy donors. The C1-INH may also be determined in "international units" ("IU"). These units are based on the current World Health Organization (WHO) standard for C1-INH concentrates (08/256) which was calibrated in an international collaborative study using normal local human plasma pools. In general, U and IU are equivalent.

The term "hereditary angioedema" ("HAE") as used herein relates to angioedema caused by a low content and low inhibitory activity of C1-INH in the circulation (HAE type I) or by the presence of normal or elevated antigenic levels of C1-INH of low functional activity (HAE type II). The term "HAE" as used herein also encompasses HAE with normal C1-INH (also known as HAE type III) which has been described recently in two subcategories: (1) HAE due to mutation in the factor XII gene and, as a result, increased activity of factor XII leading to a high generation of bradykinin, and (2) HAE of unknown genetic cause. In patients suffering from hereditary angioedema, edema attacks can occur in various intervals, including a daily, weekly, monthly, or even yearly basis. Furthermore, there are affected patients wherein no edema occurs.

The term "angioedema" ("edema") as used herein relates to swelling of tissue, for example swelling of skin or mucosa. The swelling can occur, for example, in the face, at hands or feet or on the genitals. Furthermore, swelling can occur in the gastro-intestinal tract or in the respiratory tract. Other organs can also be affected. Swelling persists usually between one and three days. However, remission can already occur after hours or not until weeks.

The term "ischemia-reperfusion injury" ("IRI") is an injury caused by the return of blood into tissue ("reperfusion") after an ischemia or a lack of oxygen. Direct damage to the tissue is caused by the interruption of the blood flow, mainly due to loss of oxygenation to the viable tissue, ultimately leading to infarction if not reversed. However, if the insult is reversed, the reperfusion of the ischemic tissue may paradoxically cause further "indirect" damage. Upon long duration of ischemia, the "direct" damage resulting from hypoxia alone is the predominant mechanism. For shorter durations of ischemia, the "indirect" reperfusion mediated damage increasingly contributes to the damage caused.

The term "retinopathy" as used herein relates to acute or persistent damage of the eye. Retinopathy can be caused by diabetes mellitus (leading to diabetic retinopathy), arterial hypertension (leading to hypertensive retinopathy), prematurity of the newborn (leading to retinopathy of prematurity), exposure to ionizing radiation (radiation retinopathy), direct sunlight exposure (solar retinopathy), sickle cell disease, retinal vascular disease such as retinal vein or artery occlusion, trauma, especially to the head and other diseases or conditions. Many types of retinopathy are proliferative resulting, most often, from neovascularization or the overgrowth of blood vessels. Angiogenesis, the sprouting of new vessels is the hallmark precursor that may result in blindness or severe vision loss particularly if the macula becomes affected. In rare cases, retinopathy is caused by genetic diseases.

The term "acute treatment" or "treatment" as used herein relates to the treatment of a patient displaying acute symptoms. Acute treatment can occur from the appearance of the symptom until the full remission of the symptom. An acute treatment can occur once or several times until the desired therapeutic effect is achieved.

The term "prophylactic treatment" or "prophylaxis" or "prevention" as used herein relates to the treatment of a patient in order to prevent the occurrence of symptoms. Prophylactic treatment can occur at regular intervals of days, weeks or months. Prophylactic treatment can also occasionally occur.

The term "about" means within an acceptable error range for a particular value, which partially depends on the limitations of the measurement system.

The term "HMWC" or "high molecular weight components" as used herein refers to any self-associated, i.e. multimerised or aggregated protein species, in particular of C1-INH, with monomer defined as the smallest functional subunit. HMWC are further classified based on five characteristics: size, reversibility/dissociation, conformation, chemical modification, and morphology (Narhi et al., J. Pharm. Sci. 2012, 101(2): 493-498).

HMWC, in particular multimers and aggregates, have been recognized for their potential to elicit immune responses to therapeutic protein products for over a half-century (Gamble, Int. Arch. Allergy Appl. Immunol. 1966, 30(5): 446-455). The underlying mechanisms by which proteins aggregate may elicit or enhance immune responses include inter alia the following: extensive cross-linking of B-cell receptors, causing efficient B-cell activation (Dintzis et al., J. Immunol. 1989, 143(4): 1239-1244; Bachmann et al., Science 1993, 262(5138): 1448-1451); enhancing antigen uptake, processing, and presentation; and triggering immunostimulatory danger signals (Seong and Matzinger, Nat. Rev. Immunol. 2004, 4(6): 469-478). Such mechanisms may enhance recruitment of the T-cell help needed for generation of high-affinity, isotype-switched IgG antibody, whereby the antibody response is most often associated with neutralization of product efficacy (Bachmann and Zinkernagel, Annu. Rev. Immunol. 1997, 15:235-70).

The term "finished dosage form (FDF)" of a drug has undergone all stages of manufacture, including packaging in its final container and labelling.

The term "physiologically acceptable salt" of this invention refers to salts in formulations that are mainly used in treating medical conditions in humans, in particular to treating or preventing disorders related to kinin formation. Further, a physiological acceptable salt refers to ionic substances which are soluble, i.e. in the liquid, preferably aqueous, state a physiological acceptable salt will be present in form of its dissolved cation(s) and anion(s), and which will not cause serious adverse side events after administration to the human body. In this sense, the formulations or their finished dosage forms are appropriate for physiological practice together with other excipients.

The term "WFI" refers to "water for injection". It is water intended for use in the manufacture of medicines for parenteral administration, the solvent of which is water. Alternatively, it refers to water that is used to dissolve or dilute substances or preparations for parenteral administration.

It is purified by distillation or a purification process, which is equivalent or superior to distillation in the removal of chemicals and microorganisms.

C1 Esterase Inhibitor

In certain embodiments of the invention, the C1-INH is a plasma-derived or a recombinant C1-INH. In further embodiments said inhibitor is identical to the naturally occurring human protein or a variant thereof. In other embodiments, said inhibitor is human C1-INH. In other embodiments, said inhibitor is a recombinant analogue of human C1-INH protein.

According to the present invention, the C1-INH may be modified to improve its bioavailability and/or half-life, to improve its efficacy and/or to reduce its potential side effects. The modification can be introduced during recombinant synthesis or otherwise. Examples for such modifications are glycosylation, PEGylation and HESylation of the C1-INH or an albumin fusion of the described C1-INH. In some embodiments, C1-INH comprises a fusion construct between C1-INH and albumin, in particular human albumin. In some embodiments, the albumin is a recombinant protein. In certain embodiments, the C1-INH and albumin proteins are joined directly, or via a linker polypeptide. For further disclosure regarding glycosylation and albumin fusion of proteins, see WO 01/79271.

Preparation of C1-INH

For the purpose of this invention, the C1-INH can be produced according to methods known to the skilled person. For example, plasma-derived C1-INH can be prepared by collecting blood plasma from several donors. Donors of plasma should be healthy as defined in the art. Preferably, the plasma of several (1000 or more) healthy donors is pooled and optionally further processed. An exemplary process for preparing C1-INH for therapeutic purposes is disclosed in U.S. Pat. No. 4,915,945. Alternatively, in other embodiments, C1-INH can be collected and concentrated from natural tissue sources using techniques known in the art. Recombinant C1-INH can be prepared by known methods.

In certain embodiments, C1-INH is derived from human plasma. In a further preferred embodiment, C1-INH is prepared by recombinant expression.

A commercially available product comprising C1-INH is, e.g., plasma-derived Berinert® (CSL Behring). Berinert® is manufactured according to A. Feussner et al. (Transfusion 2014, 54: 2566-73) and is indicated for treatment of hereditary angioedema and congenital deficiencies. Alternative commercially available products comprising C1-INH are plasma-derived Cetor® (Sanquin), Cinryze® (Shire), and recombinant Ruconest®/Rhucin® (Pharming).

C1-INH Formulations

The present invention relates to formulations comprising C1-INH. These highly concentrated formulations of the invention are provided in low volume formulations having a long-term stability. The formulations are well-tolerated and suitable for intravenous and in particular subcutaneous administration.

The concentration of C1-INH in said formulations is about 400 IU/mL to 2,000 IU/mL, preferably of about 400 IU/mL to 1,200 IU/mL, more preferably of about 400 IU/mL to 1000 IU/mL, more preferably of about 400 IU/mL to 800 IU/mL, more preferably of about 400 IU/mL to 625 IU/mL, and most preferably of about 500 IU/mL or any range in between.

Said pharmaceutical formulations of the present invention further comprise histidine, preferably L-histidine, or a salt/salts thereof at a concentration of about 5-150 mM, preferably 10-80 mM. Additionally said formulation neither comprises sodium citrate nor sodium di-hydrogen phosphate/disodium hydrogen phosphate as buffer substances.

In preferred embodiments, said formulation further comprises one or more amino acids or a salt/salts thereof. In certain embodiments the one or more amino acids are selected from arginine, glycin and/or lysine. The amino acids may be L- or D-amino acids, preferably L-amino acids. The concentration of each further amino acid of this invention ranges from about 2 mM to about 150 mM, preferably from about 3 mM to about 130 mM, more preferably from about 5 mM to about 50 mM.

In certain embodiments the pharmaceutical formulation comprises only one type of further amino acid.

In certain embodiments, the formulations referred to herein do not comprise a buffer compound selected from the following: succinate, tartrate, maleate, acetate, and salts thereof.

In further embodiments, the formulation comprises saccharose, trehalose, or a combination thereof at a concentration of about 5-250 mM, preferably at a concentration of about 20-200 mM, more preferably at a concentration of about 100-200 mM. In highly preferred embodiments, the concentration is about 140-160 mM.

In various embodiments, the pharmaceutical formulation further comprises at least one substance selected from the group consisting of sodium chloride, di-sodium EDTA, sodium acetate, sodium glutamate and sodium succinate at a concentration of about 1-200 mM, preferably of about 10-200 mM, more preferably of about 20-150 mM, and even more preferably of about 40-60 mM or about 130-150 mM.

In certain embodiments the pharmaceutical formulation does not comprise a tissue permeability enhancer, such as e.g. hyaluronidase.

In some embodiments, the pH of the formulation is between about 6.0 and 8.0, between about 6.7 and 7.5, between about 6.8 and 7.4, between about 6.9 and 7.3, between about 7.0 and 7.2. In the most preferred embodiment, the pH of the formulation is 7.0.

In some embodiments, the pharmaceutical formulation comprises
(a) C1-INH;
(b) sodium chloride;
(c) histidine; and
(d) saccharose.

In certain embodiments, the pharmaceutical formulation comprises
(a) about 400-625 IU/mL C1-INH;
(b) about 20-200 mM sodium chloride;
(c) about 10-90 mM histidine; and
(d) about 100-200 mM saccharose.

In other embodiments, the pharmaceutical formulation comprises
(a) C1-INH;
(b) sodium chloride;
(c) histidine;
(d) arginine or arginine*HCl; and
(d) saccharose.

In certain embodiments, the pharmaceutical formulation comprises
(a) about 400-625 IU/mL C1-INH;
(b) about 20-200 mM sodium chloride;
(c) about 5-150 mM histidine;
(d) about 5-50 mM arginine or arginine*HCl; and
(e) about 100-200 mM saccharose.

In preferred embodiments, the pharmaceutical formulation comprises:
(a) about 400-625 IU/mL C1-INH;
(b) about 25-70 mM sodium chloride;
(c) about 20-80 mM histidine;
(d) about 5-30 mM arginine or arginine*HCl; and
(e) about 120-160 mM saccharose.

In more preferred embodiments, the pharmaceutical formulation comprises:
(a) about 400-625 IU/mL C1-INH;
(b) about 30-60 mM sodium chloride;
(c) about 60-70 mM histidine;
(d) about 10-20 mM arginine or arginine*HCl; and
(e) about 120-160 mM saccharose.

In even more preferred embodiments, the pharmaceutical formulation comprises:
(a) about 400-625 IU/mL C1-INH;
(b) about 40-50 mM sodium chloride;
(c) about 60-70 mM histidine;
(d) about 10-15 mM arginine or arginine*HCl; and
(e) about 140-150 mM saccharose.

In further embodiments, the provided formulation comprises one or more detergents and/or one or more preservatives and/or one or more antioxidants.

In certain embodiments, the pharmaceutical formulation can comprise PS80 (polysorbate 80) and/or PS20 (polysorbate 20). In the pharmaceutical formulation, PS80 may be present at a concentration of about 0.5-2 mg/mL. In the pharmaceutical formulation, PS20 may be present at a concentration of about 0.5-2 mg/mL.

In certain embodiments, the preservatives and/or antioxidants are selected from the group consisting of benzylalcohol, cresol, phenol, methionine and glutathione. In the pharmaceutical formulation the preservatives and/or antioxidants may be present at a concentration of about 1-5 mM.

The provided formulations may comprise pharmaceutical carriers and excipients that are well known in the art (see for example "Pharmaceutical Formulation Development of Peptides and Proteins", Frokjaer et al., Taylor & Francis 2000 or "Handbook of Pharmaceutical Excipients", $3^{rd}$ edition, Kibbe et al., Pharmaceutical Press 2000).

In one embodiment, the formulation comprises an absolute amount of C1-INH of about 1,000 IU/FDF, 1,200 IU/FDF, about 1,500 IU/FDF, about 1,800 IU/FDF, about 2,100 IU/FDF, about 2,400 IU/FDF, about 2,700 IU/FDF or about 3,000 IU/FDF or any absolute amount in between. In preferred embodiments, the formulation comprises an absolute amount of C1-INH of at least 1,200 IU per FDF, 1,500 IU per FDF, or at least 1,800 IU per FDF.

In one embodiment, the formulation comprises an absolute amount of C1-INH of about 1,200 IU-3,000 IU, of about 1,200 IU-2,000 IU, of about 1,200 IU-1,800 IU or of about 1,400 IU-1,600 IU.

In one embodiment, the liquid pharmaceutical formulation is provided in a volume of about 0.1-10 mL/FDF, about 1-5 mL/FDF or about 3 mL/FDF or any volume in between. In preferred embodiments, the formulation is provided as an aqueous solution in a volume of about 3 mL per FDF, of about 4 mL per FDF or of about 6 mL per FDF.

In some embodiments, the C1-INH is human C1-INH. In certain embodiments the human C1-INH is derived from human plasma, or the human C1-INH is recombinantly expressed. Preferably, the C1-INH is derived from human plasma.

In various embodiments, the pharmaceutical formulations of the invention comprises less than 10% of HMWC, preferably less than 8% of HMWC, more preferably less than 5% of HMWC or even more preferably less than 3% of HMWC as determined immediately by SEC-HPLC. Immediately after preparation means within one day after preparation.

In some embodiments, the formulation is provided as a stable lyophilized powder. The formulation may be lyophilized by a variety of procedures known in the art. The lyophilized powder can be reconstituted with a respective volume of a suitable liquid to obtain the pharmaceutical liquid formulation for injection. Suitable liquids are, e.g., water for injection (WFI).

In alternative embodiments, the formulation is provided as a stable liquid formulation. In one embodiment, the liquid formulation is obtainable by reconstitution of a stable lyophilized powder with a suitable liquid.

In other words, in various embodiments, the components of the pharmaceutical formulation are present in a solution suitable for injection without any further processing, i.e. the formulation is provided as a stable liquid formulation. Alternatively, the components are provided as a stable lyophilized powder and the indicated concentrations are reached upon reconstitution of the lyophilized powder in the respective volume of a suitable liquid. A suitable liquid for reconstitution is e.g. water for injection (WFI).

The terms "stable formulation", "stable lyophilized powder", "stable lyophilized formulation" or "stable liquid formulation" as used herein refer to pharmaceutical formulations wherein no significant decrease of C1-INH activity is observed after a certain period of time of storage at least at 2-8° C., preferably at about 25° C. The term "no significant decrease of C1-INH activity" means at least 70%, 75%, 80%, 85%, 90%, 95% 96%, 97%, 98%, 99% of the C1-INH activity of the original C1-INH activity. The term "C1-INH activity" refers to the inhibitory activity of the C1-INH protein in plasma and is indicated in "IU/mL" and can be measured without limitation e.g. by a chromogenic assay (see e.g. example 1).

In alternative embodiments, the terms "stable formulation", "stable lyophilized powder", "stable lyophilized formulation" or "stable liquid formulation" as used herein refer to formulations wherein no significant increase of HMWC formation is observed after a certain period of time, preferably at least 36 months, of storage at 2-8° C., preferably at about 25° C. The term "no significant increase of HMWC formation" means at most 20%, 15%, 14%, 13%, 12%, 11% 10%, 9%, 8%, 7%, 6%, 5%, 4%, or about 3% protein HMWC at a certain point in time, e.g. after 1, 2, 3, 4, 5, 6, 7, 8, 9, 10 11, 12, 15, 18, 21, 24, or 36 months, i.e. the percentage of HMWC is determined as the percentage of HMWC of the total protein content in the formulation at this certain point of time and this value is at the most 20%, 15%, 14%, 13%, 12%, 11% 10%, 9%, 8%, 7%, 6%, 5%, 4%, 3%. The level of protein HMWC of the total protein can be measured without limitation e.g. by SEC HPLC (see e.g. example 1).

In further alternative embodiments the terms "stable formulation", "stable lyophilized powder", "stable lyophilized formulation" or "stable liquid formulation" as used herein refer to formulations wherein no significant increase of HMWC formation is observed after a certain period of time, preferably at least 18-24 months, of storage at about 40° C. The term "no significant increase of HMWC formation" means formation of at most 20%, 15%, 14%, 13%, 12%, 11% 10%, 9%, 8%, 7%, 6%, 5%, or about 4% protein HMWC at a certain point in time, e.g. after 1, 2, 3, 4, 5, 6, 7, 8, 9, 10 11, 12, 15, 18, 21, or 24 months, i.e. the percentage of HMWC is determined as the percentage of HMWC of the total protein content in the formulation at this certain point of time and this value is at the most 20%, 15%, 14%, 13%, 12%, 11% 10%, 9%, 8%, 7%, 6%, 5%, 4%. The level of protein HMWC of the total protein can be measured without limitation e.g. by SEC HPLC (see e.g. example 1).

In alternative embodiments, the terms "stable formulation", "stable lyophilized powder", "stable lyophilized formulation" or "stable liquid formulation" as used herein refer to formulations wherein no significant increase of fragmentation is observed after a certain period of time, preferably at least 36 months, of storage at 2-8° C., preferably at about 25° C. The term "no significant increase of fragmentation" means at most 20%, 15%, 14%, 13%, 12%, 11% 10%, 9%, 8%, 7%, 6%, 5%, 4%, or about 3% fragments at a certain point in time, e.g. after 1, 2, 3, 4, 5, 6, 7, 8, 9, 10 11, 12, 15, 18, 21, 24, or 36 months, i.e. the percentage of fragments is determined as the percentage of fragments the total protein content in the formulation at this certain point of time and this value is at the most 20%, 15%, 14%, 13%, 12%, 11% 10%, 9%, 8%, 7%, 6%, 5%, 4%, 3%. The level of fragments of the total protein can be measured without limitation e.g. by SEC HPLC.

In a series of embodiments, the formulations provided herein upon lyophilization will be stable for a certain period of time, i.e. for at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or more months at a temperature of 25° C. In a preferred embodiment, the lyophilized formulation will be stable for at least 6 months (25° C.). In a more preferred embodiment, the lyophilized formulation will be stable for at least 12 months (25° C.). In another preferred embodiment, the lyophilized formulation will be stable for at least 24 months (25° C.).

In another series of embodiments, the liquid formulation provided herein will be stable for a certain period of time, i.e. for at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 or more months at a temperature of 2-8° C. In a preferred embodiment, the liquid formulation will be stable for at least 6 months (2-8° C.). In a more preferred embodiment, the liquid formulation will be stable for at least 12 months (2-8° C.). In another preferred embodiment, the liquid formulation will be stable for at least 24 months (2-8° C.).

In another series of embodiments, the liquid formulation provided herein will be stable for a certain period of time, i.e. for at least 1, 2, 3, 4, 5, 6, 7, 8, 9, 10, 11, 12, 13, 14, 15, 16, 17, 18, 19, 20, 21, 22, 23, 24 or more months at a temperature of 25° C. In a preferred embodiment, the liquid formulation will be stable for at least 6 months (25° C.). In a more preferred embodiment, the liquid formulation will be stable for at least 12 months (25° C.).

In certain embodiments, the provided formulations retain at least 70%, preferably at least 80%, more preferably at least 90% and most preferably at least 95% C1-INH activity after 12 months, preferably after 24 months, more preferably after 36 months and most preferably after 48 months of storage at 2-8° C.

In certain embodiments, the provided formulation retains at least 70%, preferably at least 80%, more preferably at least 90% and most preferably at least 95% C1-INH activity after 6 months, preferably after 12 months, more preferably after 24 months and most preferably after 36 months of storage at 25° C.

In certain embodiments, the provided formulation retains at least 30%, preferably at least 40%, more preferably at least 50% and most preferably at least 60% C1-INH activity after 6 month, preferably after 12 months, more preferably after 24 months of storage at 40° C.

Hence, the provided pharmaceutical formulations can be utilized as stand-by medication, i.e., a patient suffering from hereditary angioedema can always keep such a formulation in close proximity (without the requirement of cooling) in order to have an immediate treatment available upon occurrence of an edema attack. Moreover, the provided pharmaceutical formulations demonstrate a long-term stability compared to concentrated C1-INH formulations having only a buffer excipient in low concentrations.

The provided pharmaceutical formulations are suitable for subcutaneous administration as well as intravenous administration. In general, subcutaneous administration is preferred upon prophylactic treatment of patients suffering from hereditary angioedema and intravenous administration is preferred upon acute treatment of patients suffering from hereditary angioedema. Neither the intravenous nor the subcutaneous administration of the provided pharmaceutical formulations causes serious drug-related adverse side events but only minor treatment-emergent adverse effects. Hence, the provided formulations can be used for both administrations. In further embodiments, the pharmaceutical formulation described herein is suitable for intra-arterial and/or intramuscular administration.

Moreover, the patients can self-administer the provided formulations.

Patients can use the provided formulations for prophylactic treatment and, in addition, the same formulation can be used for an acute treatment upon occurrence of an angioedema attack. Hence, patients are only supplied with one type of formulation, which is indicative of a high patient compliance and which can be used as required. For these reasons, the provided formulations may achieve a high patient compliance.

Furthermore, the provided formulations exhibit a high local tolerance upon subcutaneous and intravenous injection; they are well tolerated, with no serious drug-related adverse events. In particular, the subcutaneous administration of the provided formulations is safe and well tolerated with only mild-to-moderate local site reactions. Likewise, a high local tolerance is achieved upon intra-arterial injection and intramuscular injection.

Upon administration of the described formulations, no immune reaction directed against the formulation can be observed in the patient after 1, 6, 12, 24, 48 or 72 hours from the time point of administration.

Moreover, thrombotic events, clot formation, thromboembolic complications do not occur after administration of the described formulations in any of the described doses in a patient. Further, administration of the described formulations does not enhance the thrombogenic risk in a patient.

The pharmaceutical formulations of the present invention ensure a good bioavailability of the C1-INH upon subcutaneous as well as upon intravenous administration.

Moreover, periodic subcutaneous administration of the provided formulations leads to a dose-dependent increase in functional C1-INH activity, which would have a clinically meaningful effect in preventing HAE attacks. Upon subcutaneous administration of the provided formulations, C1-INH functional activity time profiles with a considerably lower peak-to-trough ratio and more consistent exposures after subcutaneous administration are achieved. These lower peak-to-trough fluctuations for the subcutaneous administration are particularly desired upon prophylactic treatment, as such plasma levels ensure persistent protection from the occurrence of angioedema attacks in patients suffering from hereditary angioedema.

In another aspect, a kit is provided comprising a lyophilized formulation described herein and the respective amount of a liquid suitable for reconstitution. In certain embodiments, the suitable liquid is water for injection, preferable deionized sterile water for injection.

In some embodiments, the kit can additionally comprise a syringe. In certain embodiments, the syringe is suitable for subcutaneous injection. In other embodiments, the syringe is suitable for intravenous injection. In alternative embodiments, the syringe is suitable for subcutaneous injection and intravenous injection. In further embodiments, the syringe is suitable for intra-arterial injection and/or intramuscular injection.

In some embodiments, the kit further can comprise a needle suitable for intravenous injection and/or a needle suitable for subcutaneous injection. In a further embodiment, the kit can comprise a needle suitable for intra-arterial injection and/or a needle suitable for intramuscular injection.

In another aspect, a syringe prefilled with the liquid formulation described herein is provided. In certain embodiments, the syringe is suitable for subcutaneous injection. In other embodiments, the syringe is suitable for intravenous injection. In alternative embodiments, the syringe is suitable for subcutaneous injection and intravenous injection. In further embodiments, the syringe is suitable for intra-arterial injection and/or intramuscular injection.

In another aspect of the invention a method of reconstituting a lyophilized formulation comprising C1-INH in a suitable solution is provided herein. Furthermore, a method for reconstituting any of the lyophilized formulations described herein is provided.

In some embodiments, the use of a lyophilized formulation comprising C1-INH for the preparation of a liquid formulation comprising C1-INH is provided. The lyophilized formulation may be any lyophilized formulation described herein.

Methods and Uses

The provided formulations can be used in the treatment of various diseases and conditions.

In some embodiments, the provided formulations can be used in the treatment and/or prevention of a disorder related to kinin formation, in particular hereditary angioedema (HAE), secondary brain edema, edema of the central nervous system, hypotensive shock, or edema during or after contacting blood with an artificial surface.

Further provided is a method of treating or preventing a disorder related to kinin formation, in particular hereditary angioedema (HAE), secondary brain edema, edema of the central nervous system, hypotensive shock, or edema during or after contacting blood with an artificial surface in a patient, comprising administering a pharmaceutically effective dose of any of the formulations described herein.

In certain embodiments, the provided formulations are used in the treatment and/or prophylaxis of hereditary angioedema, in particular HAE type I, HAE type II and/or HAE type III.

In certain embodiments, a method of treating or preventing hereditary angioedema, in particular HAE type I, HAE type II and/or HAE type III in a patient, comprising administering a pharmaceutically effective dose of any of the formulations described herein, is provided.

In further embodiments, the provided formulations can be used in the treatment and/or prophylaxis of an ischemia-reperfusion injury (IRI), in particular wherein the IRI is due to surgical intervention, in particular vascular surgery, cardiac surgery, neurosurgery, trauma surgery, cancer surgery, orthopedic surgery, transplantation, minimally invasive surgery, or insertion of a device for delivery of a pharmacologically active substance or for mechanical removal of complete or partial obstructions.

Further provided is a method of treating or preventing an ischemia-reperfusion injury (IRI), in particular wherein the IRI is due to surgical intervention, in particular vascular surgery, cardiac surgery, neurosurgery, trauma surgery, cancer surgery, orthopedic surgery, transplantation, minimally invasive surgery, or insertion of a device for delivery of a pharmacologically active substance or for mechanical removal of complete or partial obstructions in a patient, comprising administering a pharmaceutically effective dose of any of the formulations described herein.

In some embodiments, the provided formulations can be used to prevent rejection of a transplanted tissue in a patient. The transplantation can be allotransplantation or xenotransplantation.

Further provided is a method of preventing rejection of a transplanted tissue in a patient, comprising administering a pharmaceutically effective dose of any of the formulations described herein. The transplantation can be allotransplantation or xenotransplantation.

In further embodiments, the provided formulations can be used in the treatment and/or prevention of retinopathy.

Further provided is a method of treating or preventing retinopathy in a patient, comprising administering a pharmaceutically effective dose of any of the formulations described herein Treatment and Administration In various embodiments, acute treatment occurs upon treatment of a patient having hereditary angioedema and suffering from an acute angioedema attack.

In further embodiments, prophylactic treatment of a patient having hereditary angioedema occurs in order to prevent the occurrence of angioedema. Prophylactic treatment of patients suffering from hereditary angioedema can be done regularly and can also occur occasionally, for example before surgical interventions, dental treatments and other symptom-triggering situations such as a situation where a patient realizes an upcoming edema.

In various embodiments, the provided formulations can be administered via subcutaneous injection. In alternative embodiments, the provided formulations can be administered via intravenous injection. The formulations can be administered continuously by infusion or by bolus injection. In a preferred embodiment, the provided formulations can be administered via subcutaneous injection and via intravenous injection. In a further preferred embodiment, the patient can self-administer the provided formulations.

In some embodiments, the provided formulation is administered via intravenous injection during acute treatment of a patient. In other embodiments, the provided formulation is administered via subcutaneous injection during prophylactic treatment of a patient.

In further embodiments, the provided formulations can be administered via intra-arterial injection. In further embodiments, the provided formulations can be administered via intramuscular injection.

In further embodiments, the formulations described herein may be administered to a patient by any pharmaceutically suitable means of administration. Various delivery systems are known and can be used to administer the composition by any convenient route. Preferentially the compositions of the invention are administered systemically. For systemic use, the therapeutic proteins of the invention are formulated for parenteral (e.g. intravenous, subcutaneous, intramuscular, intraperitoneal, intracerebral, intrapulmonar, intranasal or transdermal) or enteral (e.g., oral, vaginal or rectal) delivery according to conventional methods. Some formulations encompass slow release systems.

Dosing Schemes

In one embodiment, a dose of C1-INH of about 1,200 IU, about 1,500 IU, about 1,600 IU, about 1,700 IU, about 1,800 IU, about 1,900 IU, about 2,000 IU, about 2,100 IU, about 2,200 IU, about 2,300 IU, about 2,400 IU, about 2,500 IU, about 2,600 IU, about 2,700 IU, about 2,800 IU, about 2,900 IU, about 3,000 IU, about 3,500 IU, about 4,000 IU, about 4,500 IU, about 5,000 IU, about 5,500 IU or about 6,000 IU or any amount in between is administered to a patient. In a preferred embodiment, a dose of about 1,500 IU, about 2,000 IU, about 3,000 IU, about 4,000 IU, about 5,000 IU or about 6,000 IU is administered to a patient.

In further embodiments, a dose of C1-INH of about 10-100 IU/kg bodyweight, of about 20-90 IU/kg bodyweight, of about 20-80 IU/kg bodyweight, of about 30-70 IU/kg bodyweight, of about 40-60 IU/kg bodyweight or any range in between is administered to a patient.

In certain embodiments, upon subcutaneous administration a dose of C1-INH of about 20-80 IU/kg bodyweight, of about 30-80 IU/kg bodyweight, of about 40-80 IU/kg bodyweight, of about 40-60 IU/kg bodyweight, of about 50-60 IU/kg bodyweight or any range in between is administered to a patient.

In certain embodiments, upon intravenous administration, preferably in the acute treatment, a dose of C1-INH of about 10-60 IU/kg bodyweight, of about 20-40 IU/kg bodyweight, of about 20 IU/kg bodyweight or any range in between is administered to a patient.

In certain embodiments the target is to reach a mean C1-INH activity level in the prophylactic treatment.

In various embodiments, a dose of C1-INH is administered, preferably in prophylactic treatment, at intervals of 1, 2, 3, 4, 5, 6 or 7 days. In a further embodiment, a dose of C1-INH is administered, preferably in prophylactic treatment, at intervals of every 1-2 days, at intervals of every 2-3 days, at intervals of every 3-4 days, at intervals of every 4-5 days, at intervals of every 5-6 days or at intervals of every 6-7 days.

In some embodiments, a formulation comprising one, two or more FDF(s) of about 1,500 IU of C1-INH is/are administered, preferably subcutaneously, at intervals of every 2-3 days.

In further embodiment, a formulation comprising one, two or more FDF(s) of about 3,000 IU of C1-INH is/are administered, preferably subcutaneously, at intervals of every 3-4 days.

In further embodiments, a formulation comprising about 1,500 IU, about 3,000 IU, about 4,000 IU, about 5,000 IU or about 6,000 IU of C1-INH is/are administered, preferably subcutaneously, weekly.

In further embodiments, a formulation comprising about 1,500 IU, about 3,000 IU, about 4,000 IU, about 5,000 IU or about 6,000 IU of C1-INH is/are administered, preferably subcutaneously, twice-weekly.

In other embodiments, a formulation comprising a dose of about 20-80 IU per kg bodyweight, preferably about 20-40 IU C1-INH per kg bodyweight is administered, preferably subcutaneously, at intervals of every 2-3 days.

In further embodiments, a formulation comprising a dose of about 40-60 IU C1-INH per kg bodyweight is administered, preferably subcutaneously, at intervals of every 3-4 days.

In further embodiments, a formulation comprising a dose of about 40-80 IU C1-INH per kg bodyweight or of about 40-60 IU C1-INH per kg bodyweight is administered, preferably subcutaneously, weekly.

In further embodiments, a formulation comprising a dose of about 40-80 IU C1-INH per kg bodyweight or of about 40-60 IU C1-INH per kg bodyweight is administered, preferably subcutaneously, twice weekly.

In other embodiments, one, two or more FDF(s) of about 1,500 IU C1-INH is/are administered to a patient during acute treatment, preferably via intravenous administration. In a further embodiment, one or more FDF(s) of about 3,000 IU C1-INH is/are administered to a patient during acute treatment, preferably via intravenous administration.

In further embodiments, one, two or more dose(s) of about 20 IU C1-INH per kg bodyweight is/are administered to a patient during acute treatment, preferably via intravenous administration. In a further embodiment, one or more dose(s) of about 40 IU C1-INH per kg bodyweight is/are administered to a patient during acute treatment, preferably via intravenous administration.

The examples illustrate the present invention while in no way limiting it.

Example 1

Figure 1:
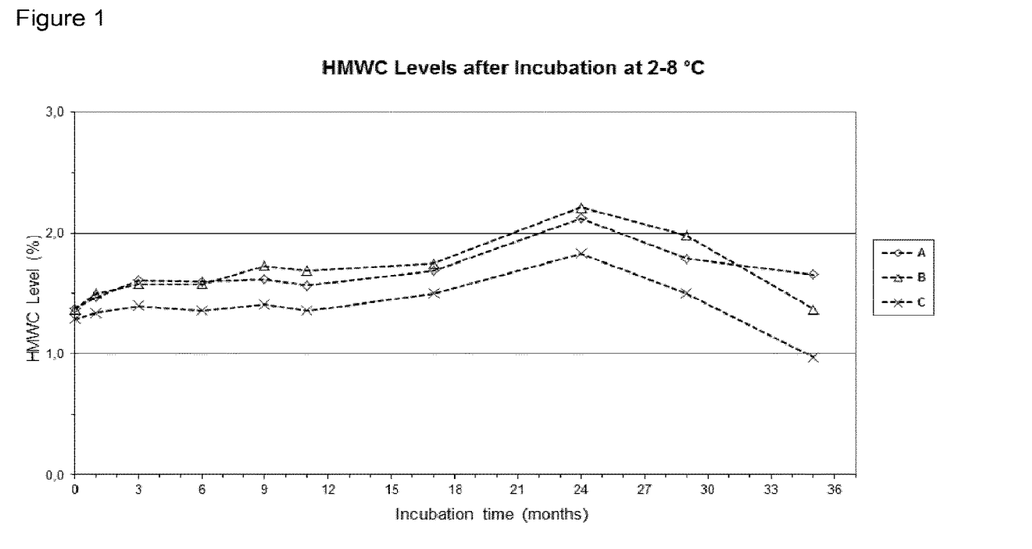
FIG. 1: HMWC levels by SEC HPLC of three C1-INH formulations over 36 months at 2-8° C.
Figure 2:
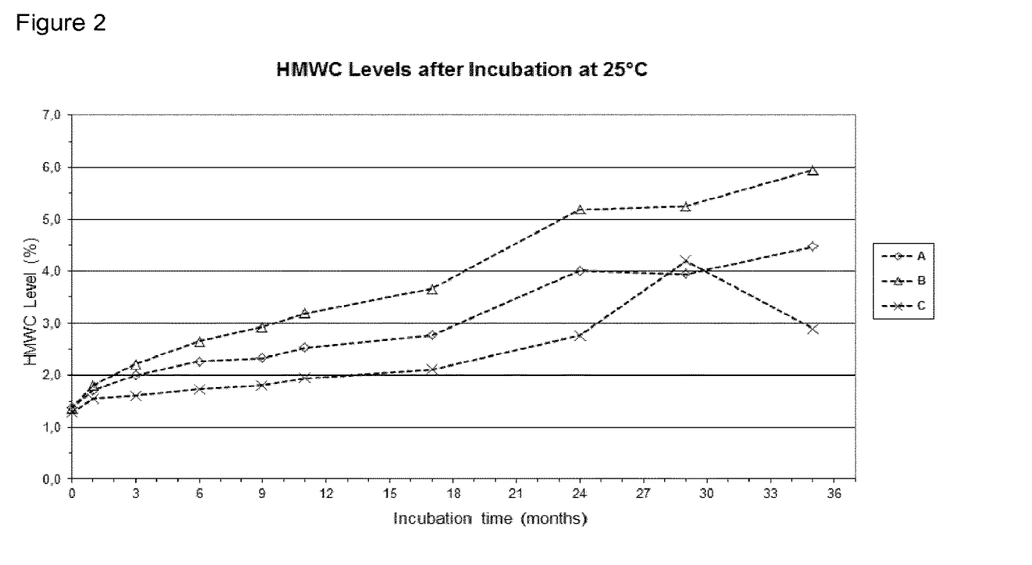
FIG. 2: HMWC levels by SEC HPLC of three C1-INH formulations over 36 months at 25° C.
Figure 3:
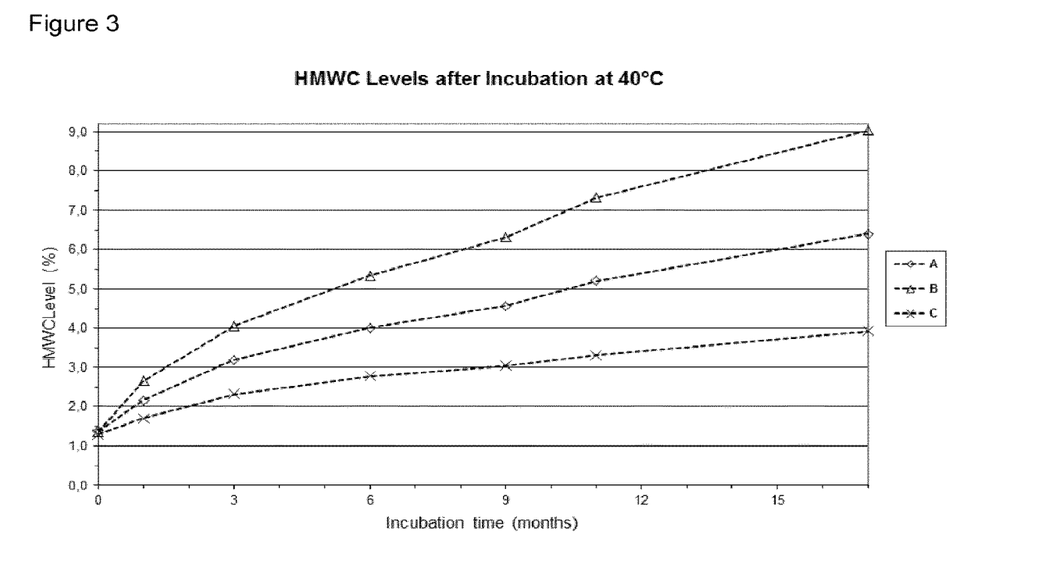
FIG. 3: HMWC levels by SEC HPLC of three C1-INH formulations over 18 months at 40° C.
Figure 4:
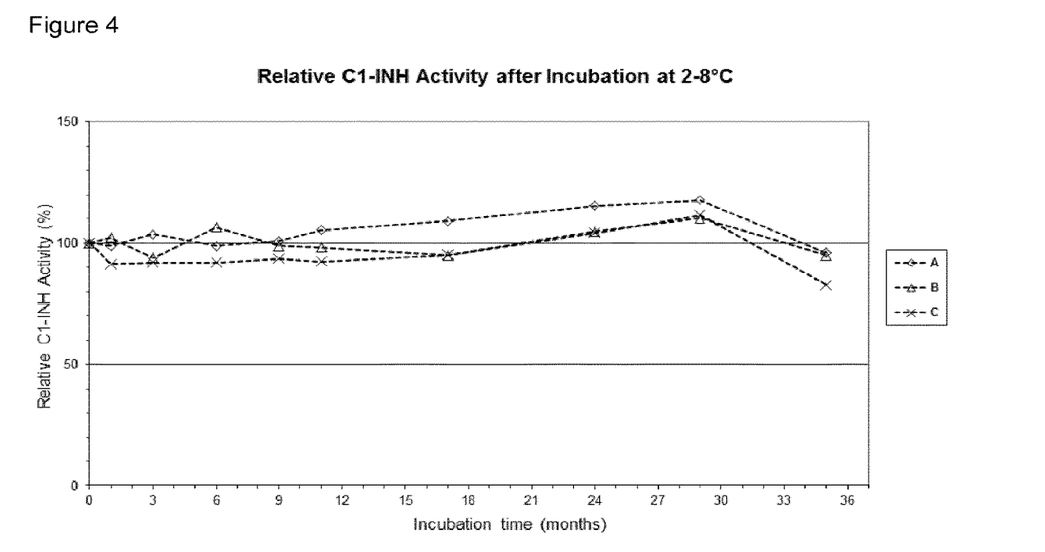
FIG. 4: Relative C1-INH activity of three C1-INH formulations over 36 months at 2-8° C.
Figure 5:
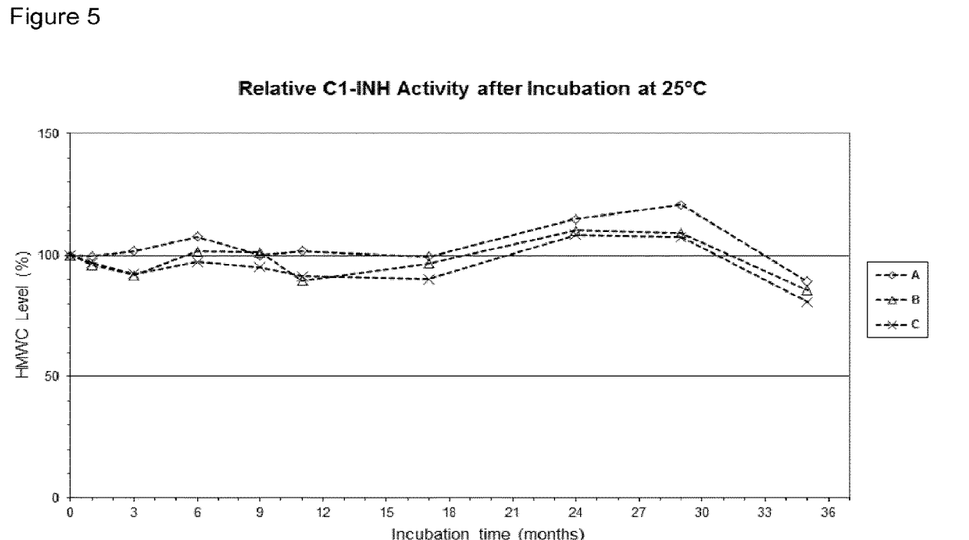
FIG. 5: Relative C1-INH activity of three C1-INH formulations over 36 months at 25° C.
Figure 6:
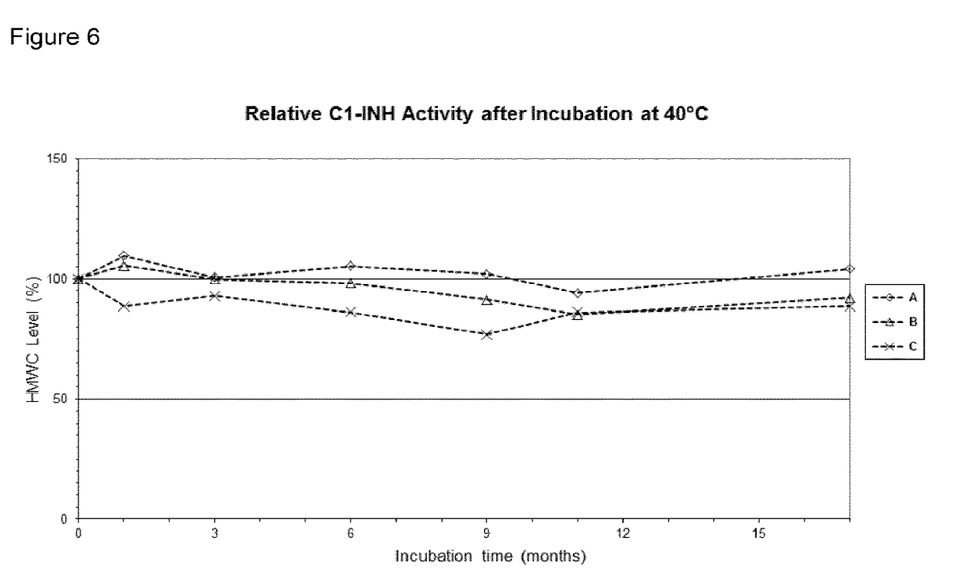
FIG. 6: Relative C1-INH activity of three C1-INH formulations over 18 months at 40° C.
Figure 7:
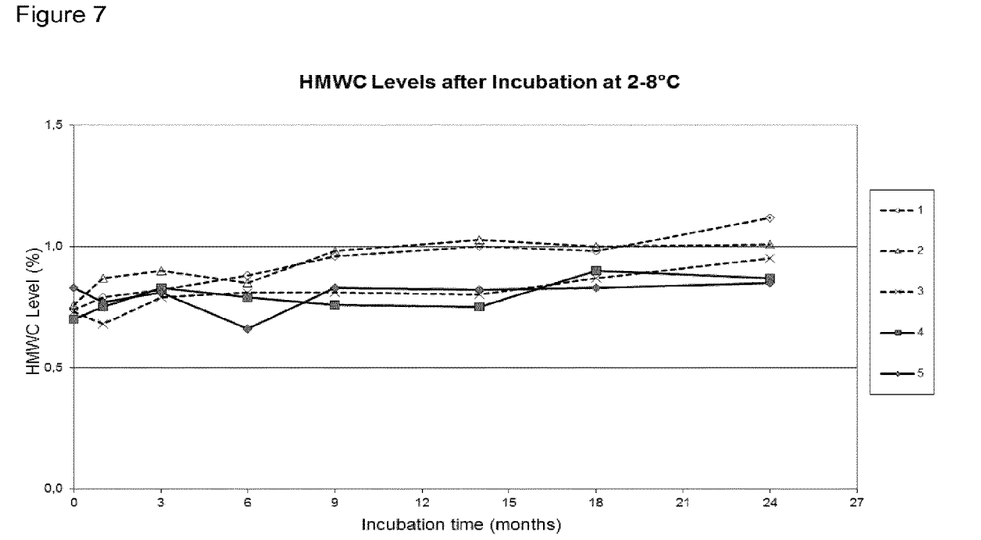
FIG. 7: HMWC levels by SEC HPLC of five C1-INH formulations over 24 months at 2-8° C.
Figure 8:
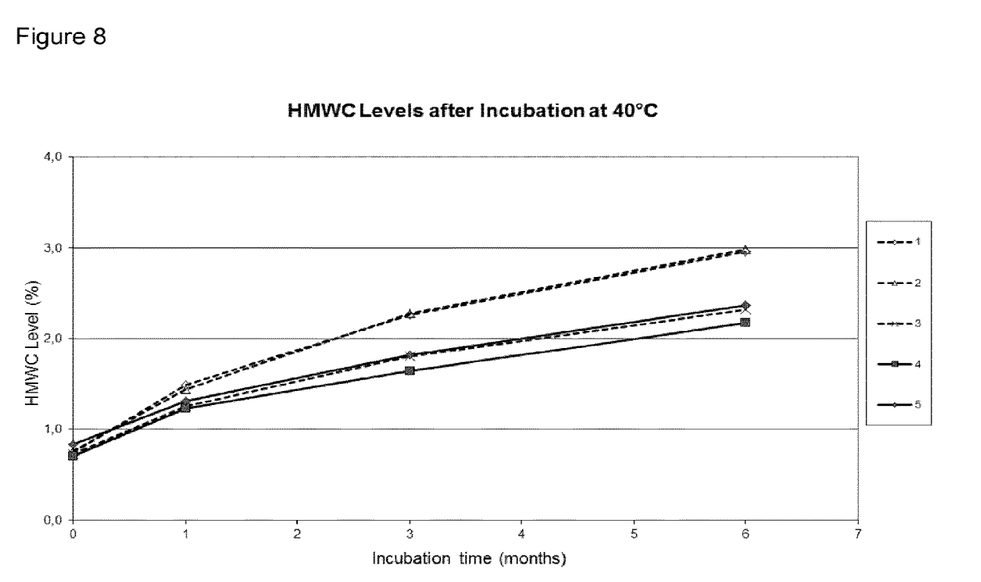
FIG. 8: HMWC levels by SEC HPLC of five C1-INH formulations over 6 months at 40° C.
Figure 9:
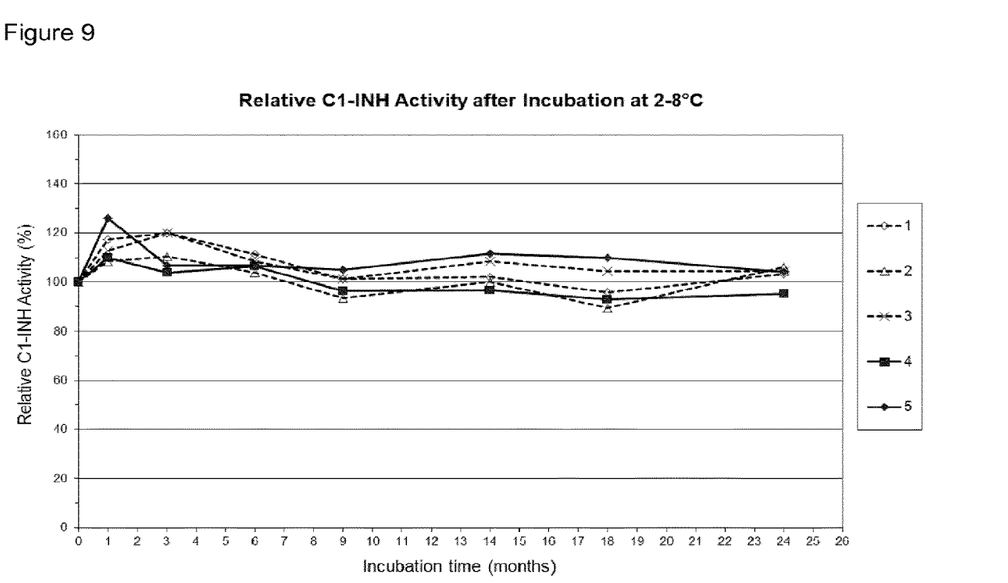
FIG. 9: Relative C1-INH activity of five C1-INH formulations over 24 months at 2-8° C.
Figure 10:
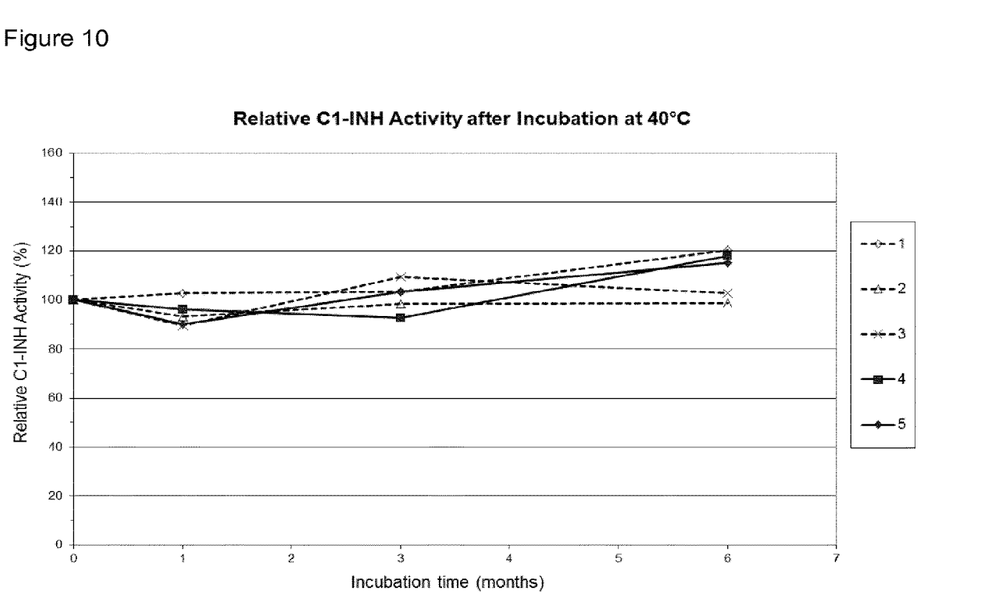
FIG. 10: Relative C1-INH activity of five C1-INH formulations over 6 months at 40° C.

Freeze dried C1-INH concentrate (manufactured based on the Berinert® manufacturing process (according to A. Feussner et al., Transfusion 2014, 54: 2566-73)) was dissolved in WFI. PD10 desalting columns (GE Healthcare)

were equilibrated with the target formulation buffer. Then the C1-INH solutions were applied per PD10 column. C1-INH was eluted with the corresponding formulation buffer (see Tables 1 and 2) within the column exclusion volume. C1-INH concentration was determined by chromogenic assay (Berichrom C1-Inhibitor, Siemens) and adjusted to 500 IU/ml using the corresponding formulation buffer. Formulated C1-INH was filtered through 0.2 μm and then dispensed in aliquots to glass vials, lyophilized and then stoppered with rubber stoppers under aseptic conditions. This was done for each of the different C1-INH formulations disclosed in Table 1 and 2. The respective glass vials were finally transferred to tempered rooms at 2-8° C., 25° C. or 40° C. (Table 1) and 2-8° C. or 40° C. (Table 2). Sample vials of each C1-INH formulation were taken at various time points and tested for C1-INH activity by chromogenic assay and for HMWC formation and fragmentation by SEC HPLC on a TSK-Gel G3000SWXL (Tosoh) using 20 mM $NaH_2PO_4$, 20 mM $Na_2HPO_4$, 100 mM NaCl, pH 7.2 as eluent buffer (see FIGS. 1 to 10).

TABLE 1

C1-INH formulations A, B, and C.

| Formulation | | A | B | C |
|---|---|---|---|---|
| C1-INH | [IU/mL]* | 500 | 500 | 500 |
| NaCl | [g/L] | 8.5 | 4.0 | 2.5 (~43 mM) |
| Glycin | [g/L] | 10.0 | 10.0 | — |
| $Na_3$citrat*$2H_2O$ | [g/L] | 3.5 | 3.5 | — |
| Histidin | [g/L] | — | — | 10.0 (~65 mM) |
| Arginin*HCl | [g/L] | — | — | 2.0 (~12 mM) |
| Saccharose | [g/L] | — | — | 50.0 (~146 mM) |
| pH | | 7.0 | 7.0 | 7.0 |
| Resid. Moisture | [%] | 0.21 | 0.18 | 0.16 |

*C1-INH concentration after reconstitution of the respective formulation with 1 mL WFI Results of the formulations A to C of Table 1 are demonstrated in FIGS. 1 to 6. These data indicate for the formulation C the best C1-INH activity conservation and the lowest HMWC formation.

TABLE 2

C1-INH formulations 1 to 5.

| Formulation | | 1 | 2 | 3 | 4 | 5 |
|---|---|---|---|---|---|---|
| C1-INH | [IU/mL]* | 500 | 500 | 500 | 500 | 500 |
| NaCl | [g/L] | 8.5 (~145 mM) | 8.5 (~145 mM) | — | — | — |
| Glycin | [g/L] | 10.0 (~133 mM) | 10.0 (~133 mM) | — | — | — |
| Histidin | [g/L] | 2.0 (~13 mM) | 2.0 (~13 mM) | 10.0 (~65 mM) | 10.0 (~65 mM) | 10.0 (~65 mM) |
| Arginin*HCl | [g/L] | — | — | — | 2.0 (~12 mM) | — |
| Saccharose | [g/L] | — | — | 50.0 (~146 mM) | 50.0 (~146 mM) | 50.0 (~146 mM) |
| pH | | 7.0 | 8.0 | 7.0 | 7.0 | 8.0 |

*C1-INH concentration after reconstitution of the respective formulation with 1 mL WFI Results of the formulations shown in Table 2 are demonstrated in FIGS. 7 to 10. These data indicate for all five formulations acceptable long term stabilities.

The invention claimed is:

1. A pharmaceutical formulation comprising
   (a) C1-INH at a concentration of about 400 IU/mL to 2,000 IU/mL; and
   (b) histidine or a salt thereof at a concentration of about 5 mM to 150 mM,
   wherein the formulation does not comprise citrate or phosphate, and
   wherein the pH of the formulation is between about 6.7 and 7.5.

2. The pharmaceutical formulation according to claim 1, further comprising one or more additional amino acid, or a salt thereof, at a concentration of 2 mM to 150 mM for each amino acid.

3. The pharmaceutical formulation according to claim 2, wherein said one or more additional amino acid comprises one or more of arginine, glycine, lysine, and a salt thereof.

4. The pharmaceutical formulation according to claim 1, further comprising saccharose at a concentration of about 5-250 mM.

5. The pharmaceutical formulation according to claim 1, further comprising sodium chloride or sodium glutamate or both at a concentration of about 1 mM to 200 mM.

6. The pharmaceutical formulation according to claim 1, wherein the formulation comprises
   (a) about 400 IU/mL to 625 IU/mL C1-INH,
   (b) about 10 mM to 200 mM sodium chloride,
   (c) about 5 mM to 150 mM histidine,
   (d) about 5 mM to 50 mM arginine or arginine*HCl, and
   (e) about 100 mM to 200 mM saccharose.

7. The pharmaceutical formulation according to claim 1, wherein the formulation further comprises
   (a) a non-ionic detergent selected from the group consisting of polysorbate 80, polysorbate 20, and a combination thereof; and/or
   (b) a preservative and/or antioxidant selected from the group consisting of benzyl alcohol, cresol, phenol, methionine glutathione, and a combination thereof.

8. The pharmaceutical formulation according to claim 1, wherein the C1-INH is (a) human C1-INH derived from human plasma or (b) human C1-INH that is recombinantly expressed.

9. The pharmaceutical formulation according to claim 1, wherein the formulation is
   (a) reconstituted from a lyophilized powder with a suitable liquid, or
   (b) provided as a liquid formulation.

10. The pharmaceutical formulation according to claim 1, wherein the formulation is provided as a lyophilized powder.

11. The pharmaceutical formulation according to claim 1, formulated for subcutaneous administration or intravenous administration.

12. A method of acute and/or prophylactic treatment of a disease or disorder, comprising administering a pharmaceutically effective amount of the pharmaceutical formulation according to claim 1 to a patient in need thereof, wherein the disease or disorder is a disorder related to kinin formation, a disorder related to ischemia-reperfusion injury (IRI), or retinopathy.

13. A kit comprising the pharmaceutical formulation according to claim 1 as a lyophilized powder and a volume of a suitable liquid for reconstitution.

14. A kit comprising the pharmaceutical formulation according to claim 1 and at least one syringe and/or one needle.

15. A syringe prefilled with a liquid pharmaceutical formulation according to claim 1.

16. The pharmaceutical formulation according to claim 1, further comprising:
   (a) one or more additional amino acid or a salt thereof, at a concentration of about 5 mM to 50 mM;
   (b) saccharose at a concentration of about 20 mM to 200 mM; and
   (c) sodium chloride and/or sodium glutamate at a concentration of about 20 mM to 150 mM;
   wherein the concentration of histidine, or a salt thereof, is about 10 mM to 80 mM.

* * * * *

UNITED STATES PATENT AND TRADEMARK OFFICE
CERTIFICATE OF CORRECTION

PATENT NO. : 11,554,156 B2
APPLICATION NO. : 16/932919
DATED : January 17, 2023
INVENTOR(S) : Hubert Metzner et al.

It is certified that error appears in the above-identified patent and that said Letters Patent is hereby corrected as shown below:

On the Title Page

Foreign Application Priority Data, "16183030" should read as --16183030.2--.

Signed and Sealed this
Twenty-eighth Day of February, 2023

Katherine Kelly Vidal
*Director of the United States Patent and Trademark Office*